(12) United States Patent
Higashi

(10) Patent No.: US 7,696,991 B2
(45) Date of Patent: Apr. 13, 2010

(54) METHOD AND APPARATUS FOR ANALYZING TWINNED CRYSTAL

(75) Inventor: Tsuneyuki Higashi, Hamura (JP)

(73) Assignee: Rigaku Corporation, Akishima-Shi (JP)

( * ) Notice: Subject to any disclaimer, the term of this patent is extended or adjusted under 35 U.S.C. 154(b) by 826 days.

(21) Appl. No.: 11/471,947

(22) Filed: Jun. 21, 2006

(65) Prior Publication Data

US 2007/0005268 A1 Jan. 4, 2007

(30) Foreign Application Priority Data

Jun. 24, 2005 (JP) ............................. 2005-184891

(51) Int. Cl.
*G06T 15/00* (2006.01)
(52) U.S. Cl. ..................................... 345/419
(58) Field of Classification Search ................ None
See application file for complete search history.

(56) References Cited

U.S. PATENT DOCUMENTS

| | | | | |
|---|---|---|---|---|
| 5,178,998 A | * | 1/1993 | Maskasky et al. | 430/569 |
| 5,846,638 A | * | 12/1998 | Meissner | 428/220 |
| 7,035,374 B2 | * | 4/2006 | Chen | 378/84 |
| 7,449,134 B2 | * | 11/2008 | Izumi et al. | 252/582 |
| 2003/0009316 A1 | * | 1/2003 | Yokoyama et al. | 703/2 |
| 2006/0032433 A1 | * | 2/2006 | Sakata | 117/89 |

FOREIGN PATENT DOCUMENTS

| | | |
|---|---|---|
| JP | 09-097278 A | 4/1997 |
| JP | 2000-039409 A | 2/2000 |
| JP | 2003-098124 A | 4/2003 |
| JP | 2003-294656 A | 10/2003 |
| JP | 3541519 B2 | 4/2004 |

OTHER PUBLICATIONS

Twinlaw and HKLF5, two programs for the handling of non-merohedral twins, Michael Bolte, Journal of Applied Crystallography (2004). 37, 162-165.
Twinning Workshop, AsCA/Crystal 23, Instructor: Victor G. Young, Jr., University of Minnesota, 14:00-16:00 Aug. 11, 2003, title page, schedule, pp. 1-14, Figs. 1-4, and attachment pp. 1-15.

(Continued)

*Primary Examiner*—Ulka Chauhan
*Assistant Examiner*—Said Broome
(74) *Attorney, Agent, or Firm*—Frishauf, Holtz, Goodman & Chick, P.C.

(57) ABSTRACT

A method and an apparatus for analyzing a twinned crystal can display three-dimensionally the real space unit lattice, the reciprocal space primitive lattices and the reciprocal lattice points of each component of the twinned crystal. Respective crystal orientation matrices of the plural components of the twinned crystal are obtained with the use of X-ray single crystal structure analytical equipment. The first computing means finds the real-space unit lattices of the plural components based on the crystal orientation matrices and creates display data for displaying them three-dimensionally with possible their rotation, scaling up and down and translation. The second computing means finds the reciprocal-space primitive lattices and creates display data for displaying them three-dimensionally. The third computing means creates display data for displaying three-dimensionally reciprocal lattice points causing X-ray diffraction with a distinction between the components of the twinned crystal.

18 Claims, 23 Drawing Sheets

OTHER PUBLICATIONS

Japanese Office Action dated Jun. 5, 2007, issued in counterpart Japanese Application No. 2005-184891, and an English language summary thereof.

Japanese Office Action dated Jan. 22, 2008, issued in counterpart Japanese Application No. 2005-184891, and an English language summary thereof.

* cited by examiner

FIG. 1

Crystal orientation matrix of twin component "i"

$$UB_i = \begin{pmatrix} m^i_{11} & m^i_{12} & m^i_{13} \\ m^i_{21} & m^i_{22} & m^i_{23} \\ m^i_{31} & m^i_{32} & m^i_{33} \end{pmatrix} \quad (1)$$

Inverse matrix of transposed crystal orientation matrix $$[(UB_i)^T]^{-1} = \begin{pmatrix} n^i_{11} & n^i_{12} & n^i_{13} \\ n^i_{21} & n^i_{22} & n^i_{23} \\ n^i_{31} & n^i_{32} & n^i_{33} \end{pmatrix} \quad (2)$$

Coordinates of real lattice vectors $$a_i = (n^i_{11} \quad n^i_{21} \quad n^i_{31}) \quad (3)$$

$$b_i = (n^i_{12} \quad n^i_{22} \quad n^i_{32}) \quad (4)$$

$$c_i = (n^i_{13} \quad n^i_{23} \quad n^i_{33}) \quad (5)$$

Coordinates of reciprocal lattice vectors $$a^*_i = (m^i_{11} \quad m^i_{21} \quad m^i_{31}) \quad (6)$$

$$b^*_i = (m^i_{12} \quad m^i_{22} \quad m^i_{32}) \quad (7)$$

$$c^*_i = (m^i_{13} \quad m^i_{23} \quad m^i_{33}) \quad (8)$$

FIG. 3

Coordinates of apexes of real-space unit lattice

Point O   Origin $(0\ \ 0\ \ 0)$ (9)

Point A   $a_i = (n^i_{11}\ \ n^i_{21}\ \ n^i_{31})$ (10)

Point B   $b_i = (n^i_{12}\ \ n^i_{22}\ \ n^i_{32})$ (11)

Point C   $c_i = (n^i_{13}\ \ n^i_{23}\ \ n^i_{33})$ (12)

Point D   $a_i + b_i = (n^i_{11}+n^i_{12}\ \ n^i_{21}+n^i_{22}\ \ n^i_{31}+n^i_{32})$ (13)

Point E   $b_i + c_i = (n^i_{12}+n^i_{13}\ \ n^i_{22}+n^i_{23}\ \ n^i_{32}+n^i_{33})$ (14)

Point F   $a_i + c_i = (n^i_{11}+n^i_{13}\ \ n^i_{21}+n^i_{23}\ \ n^i_{31}+n^i_{33})$ (15)

Point G   $a_i + b_i + c_i$ $= (n^i_{11}+n^i_{12}+n^i_{13}\ \ n^i_{21}+n^i_{22}+n^i_{23}\ \ n^i_{31}+n^i_{32}+n^i_{33})$ (16)

FIG. 4

Coordinate of reciprocal lattice point of twin component "i"

$$\begin{pmatrix} x_i \\ y_i \\ z_i \end{pmatrix} = UB_i \begin{pmatrix} h \\ k \\ l \end{pmatrix} \qquad (17)$$

Distance between reciprocal lattice points $$\Delta_{ij} = \sqrt{(x_i - x_j)^2 + (y_i - y_j)^2 + (z_i - z_j)^2} \qquad (18)$$

Distance between reciprocal lattice point and reciprocal origin $$d^*_i = \sqrt{x_i^2 + y_i^2 + z_i^2} \qquad (19)$$

Observable reflection $$d^*_i < d^*_{max} \qquad (20)$$

Upper and lower limits of reflection index (hkl)

$$-(d^*_{max} \cdot a) < h < (d^*_{max} \cdot a) \qquad (21)$$

$$-(d^*_{max} \cdot b) < k < (d^*_{max} \cdot b) \qquad (22)$$

$$-(d^*_{max} \cdot c) < l < (d^*_{max} \cdot c) \qquad (23)$$

FIG. 5

Crystal orientation matrix of twin component 1

$$UB_1 = \begin{pmatrix} -0.0177 & 0.0667 & 0.0392 \\ -0.0009 & -0.0466 & 0.0497 \\ 0.2695 & 0.0161 & 0.0080 \end{pmatrix} \quad (24)$$

Crystal orientation matrix of twin component 2

$$UB_2 = \begin{pmatrix} -0.1008 & -0.0680 & -0.0377 \\ 0.0083 & 0.0446 & -0.0508 \\ 0.2506 & -0.0161 & -0.0079 \end{pmatrix} \quad (25)$$

Interrelation matrix between twin components 1 and 2

$$R = \begin{pmatrix} -0.9017 & -0.0056 & -0.4323 \\ -0.0061 & -0.9997 & 0.0257 \\ -0.4323 & 0.0258 & 0.9014 \end{pmatrix} \quad (26)$$

- ⊙ Reciprocal lattice point of twin component 1
- ○ Reciprocal lattice point of twin component 2
- ● Overlapping reciprocal lattice points ⊚ Reciprocal lattice point of twin component 1
○ Reciprocal lattice point of twin component 2

TLQS, n=1

TLQS, n>1

TLS, n=1

TLS, n>1

METHOD AND APPARATUS FOR ANALYZING TWINNED CRYSTAL

BACKGROUND OF THE INVENTION

1. Field of the Invention

The present invention relates to a method and an apparatus for analyzing a twinned crystal with the use of X-ray single crystal structure analytical equipment using an X-ray diffraction method and for displaying the analytical result three-dimensionally.

2. Description of the Related Art

Single crystal structure analysis using the X-ray diffraction method requires high-accurate measurement of intensities of diffraction spots which are recorded in an X-ray detector. If a sample is a single crystal, it is easy to determine diffraction spot intensities with a high accuracy with the use of the ordinary X-ray single crystal structure analytical equipment. On the other hand, when a sample is a twinned crystal, especially when classified to non-merohedral twin, appearance of diffraction spots depends upon the geometrical relationship between the twin components, resulting in that, on the X-ray detector, diffraction spots coming from different twin components may overlap perfectly or partially each other. In this case, it is difficult to determine diffraction spot intensities with a high accuracy and therefore it is difficult to execute crystal structure analysis. In some cases, structural analysis would become impossible. Thus, the most important consideration in the analysis of the diffraction data on the X-ray detector is the degree of overlap of the diffraction spots on the X-ray detector. Accordingly, it is very important to understand the relationship between twin components and the degree of overlap of the reciprocal lattice points.

The term "twinned crystal" means a crystal made of two or more single crystal components joined with each other. It would be impossible in general to divide mechanically the twin crystal into its components. FIG. 17A is a perspective view of one example of the twinned crystal made of two twin components, and FIG. 17B is a perspective view of another example of the twinned crystal made of two twin components. When such a twinned crystal is studied using the structural analysis based on the X-ray diffraction method, especially when the crystal is classified to the non-merohedral twin, there appear two types of diffraction spots: one type has diffraction spots which come from reciprocal lattice spots overlap each other in reciprocal space and thus are not separable on the X-ray detector, and other type has diffraction spots which are separable on the X-ray detector. Under the circumstances, when X-ray diffraction intensities are measured and thereafter analyzed, it may become difficult to execute the structure analysis if the geometrical relationship between the twin components is not properly understood.

Some methods have been known for expressing the geometrical relationship between components consisting of a twinned crystal. The first method is to mathematically express the relationship between the twin components with the use of a three-row, three-column matrix. The second method is to display, in reciprocal space, the respective reciprocal lattice points coming from the twin components. FIGS. 18A to 18D show prior art expressions displaying two-dimensionally two nets of the reciprocal lattice points coming from two twin components, the two nets overlapping each other. Four kinds of expressions are shown depending upon the symmetrical type of the twinned crystal. FIGS. 18A and 18B show two types belonging to TLQS (Twin Lattice Quasi-Symmetry), while FIGS. 18C and 18D show other two types belonging to TLS (Twin Lattice Symmetry). FIG. 19 shows an expression displaying two-dimensionally the respective real-space unit lattices of two twin components in a two-dimensional plane. This twinned crystal has a specific relationship in which 90-degree rotation of the unit lattice ($a_1, b_1$) of the first twin component around c-axis allows it to coincide with the unit lattice ($a_2, b_2$) of the second twin component. FIG. 20 shows an expression displaying X-ray diffraction spots corresponding to the real-space unit lattices shown in FIG. 19 in a two-dimensional reciprocal lattice plane. X-ray diffraction spots coming from the first twin component are denoted by black circles, while X-ray diffraction spots coming from the second twin component are denoted by white circles.

The method of mathematically expressing the relationship between the twin components with the use of the three-row, three-column matrix is disclosed in TWINLAW and HKLF5, two programs for the handling of non-merohedral twins, Michael Bolte, Journal of Applied Crystallography, (2004). 37, 162-165. The methods of displaying the twinned crystal shown in FIGS. 18A to 18D and FIGS. 19 and 20 are disclosed in TWINNING WORKSHOP, AsCA/Crystal 23, Instructor: Victor G. Young, Jr., University of Minesota, 14:00-16:00, 11 Aug. 2003.

The above-described prior art methods for expressing the twinned crystal are inadequate to simply express the three-dimensional relationship between the twin components. The mathematical method using the matrix can define exactly the relationship between the twin components, but it is very difficult to understand the three-dimensional relationship between the twin components based on the matrix. The method of expressing the twinned crystal on the two-dimensional reciprocal lattice net as shown in FIGS. 18A to 18D and FIG. 20 would be useful, only for a scholar of crystallography having considerable knowledge and experience, to understand the three-dimensional relationship between the twin components.

SUMMARY OF THE INVENTION

It is an object of the present invention to provide a method and an apparatus for analyzing a twinned crystal with which even persons not familiar with crystallography can easily understand the relationship between the twin components and thus X-ray structural analysis of a twin crystal sample becomes more successful.

A twinned crystal analytical apparatus according to the present invention is characterized in that a twinned crystal sample is analyzed with the use of the X-ray diffraction method and its analytical result is displayed on a screen in an easy-to-understand format. The twinned crystal analytical apparatus has X-ray single crystal structure analytical equipment which measures a sample with the use of the X-ray diffraction method and analyzes the measured result. When the sample consists of plural twin components, the X-ray single crystal structure analytical equipment can find the respective crystal orientation matrices of the twin components based on the diffraction measurement result. If the crystal orientation matrices are properly found, sample analysis can be completed. In the twinned crystal case, however, an analytical operation would be difficult because of overlap of the diffraction spots as compared with the ordinary single crystal. It is not known in general whether or not the sample is a twinned crystal. When the single crystal structural analysis is carried out assuming that the sample is the ordinary single crystal, an operator sometimes obtains strange analytical result. At this moment, the operator suspects that the sample may be a twinned crystal. Under the circumstances, it is required to repeat an operation of finding the crystal orientation matrices on the assumption of a twinned crystal and an operation of displaying the analytical result on a screen. The first through the third computing means in the present invention are useful for such operations. The present invention can find crystal orientation matrices and can display three-dimensionally the relationship between components of a twinned crystal in an easy-to-understand format based on the found matrices. The first computing means creates display data for displaying three-dimensionally the respective real-space unit lattices of the twin components with an alterable viewpoint on a screen expressing three-dimensional real space. The second computing means creates display data for displaying three-dimensionally the respective reciprocal-space primitive lattices of the twin components with an alterable viewpoint on a screen expressing three-dimensional reciprocal space. The third computing means creates display data for displaying three-dimensionally reciprocal lattice points causing X-ray diffraction among the found respective reciprocal lattice points of the twin components, with a distinction between the components of the twinned crystal, with an alterable viewpoint on the screen expressing the three-dimensional reciprocal space.

Displaying with a distinction between the twin components may be displaying with different colors between the twin components. In such a case, when diffraction spots coming from different twin components overlap each other, overlapped diffraction spots may be displayed with a color different from the colors of the twin components, so that the different color can draw off operator's attention to overlapped diffraction spots.

Displaying with an alterable viewpoint may be various manners. The most important one is to alter a direction of seeing an object, i.e., to alter a visual axis. Seeing an object from various directions is effective in understanding the relationship between the twin components. Altering the visual axis corresponds to rotation of a picture object around a certain axis on a screen. Each of the first through third computing means has the function of altering the visual axis, i.e., the function of rotating a picture object, so that an operator can look at, from various directions, the real-space unit lattices, the reciprocal-space primitive lattices and the reciprocal lattice points causing X-ray diffraction.

Another manner of displaying with an alterable viewpoint may be scaling up and down of a picture object, which is convenient especially in observing the degree of overlap of diffraction spots, i.e., overlap of the reciprocal lattice points causing X-ray diffraction. Therefore, at least the third computing means preferably has the function of scaling up or scaling down of the diffraction spots, i.e., the function of altering a ratio of the magnitude of a reciprocal lattice vector to the size of the screen. With this function, diffraction spots appearing in a certain region of the reciprocal space can be displayed in a magnified form, so that an operator can look at the degree of overlap of the diffraction spots coming from the respective twin components. Further, displaying in a scale-down form allows an operator to observe the overall distribution of the diffraction spots. The first and second computing means similarly may have the function of scaling up or scaling down, which corresponds, in the first computing means, the function of altering a ratio of the magnitude of a real lattice vector to the size of the screen, and which corresponds, in the second computing means, the function of altering a ratio of the magnitude of a reciprocal lattice vector to the size of the screen as in the third computing means.

Further another manner of displaying with an alterable viewpoint may be translating a picture object on a screen, which is also convenient especially in observing the degree of overlap of diffraction spots. Therefore, at least the third computing means preferably has the function of translating the diffraction spots, i.e., the function of altering the position of the origin of the reciprocal space relative to the center of a screen. With this function, an operator can select a region of the reciprocal space to be observed. The first and second computing means similarly may have the function of translation.

The twinned crystal analytical apparatus according to the present invention has an advantage that the real-space unit lattices, the reciprocal-space primitive lattices and diffraction spots (i.e., the reciprocal lattice points causing X-ray diffraction) of the twin components are displayed three-dimensionally with an alterable viewpoint based on the respective crystal orientation matrices of the twin components found by the X-ray single crystal structure analytical equipment, and thus persons not familiar with crystallography can understand the relationship between the twin components, especially the degree of overlap of the reciprocal lattice points. Accordingly, interpreting and analyzing observed diffraction spots can be carried out in consideration of the three-dimensional relationship between the twin components, so that X-ray structural analysis of a twin crystal sample becomes more successful.

BRIEF DESCRIPTION OF THE DRAWINGS

FIG. 1 shows mathematical expressions of twin components;

FIG. 3 shows mathematical expressions regarding the coordinates of the apexes of the real-space unit lattice;

FIG. 4 shows mathematical expressions regarding the reciprocal lattice points of the twin components;

FIG. 5 shows values of the crystal orientation matrices of measured twin components;

DETAILED DESCRIPTION OF THE PREFERRED EMBODIMENTS

Embodiments of the present invention will now be described in detail below with reference to the drawings. First of all, there will be explained a method of depicting real-space unit lattices and reciprocal-space primitive lattices based on the crystal orientation matrices, provided that the respective crystal orientation matrices of the plural components of a twinned crystal are known. The crystal orientation matrix $UB_i$ of a twin component "i" is expressed by a three-row, three-column matrix as shown in equation (1) in FIG. 1. A twinned crystal sample consisting of two components has two crystal orientation matrices, i.e., i=1 and i=2. The inverse matrix of the transposed crystal orientation matrix is expressed by equation (2) in FIG. 1. The unit lattice in real space (i.e., real-space unit lattice) of the twin component "i" is expressed by a set of the real lattice vectors and the coordinates of the real lattice vectors are expressed by equations (3) thorough (5) in FIG. 1. The set of the real lattice vectors corresponds to the inverse matrix of the transposed crystal orientation matrix. The primitive lattice in reciprocal space (i.e., reciprocal-space primitive lattice) of the twin component "i" is expressed by a set of the reciprocal lattice vectors and the coordinates of the reciprocal lattice vectors are expressed by equations (6) through (8) in FIG. 1. The set of the reciprocal lattice vectors corresponds to the crystal orientation matrix.

Figure 2:
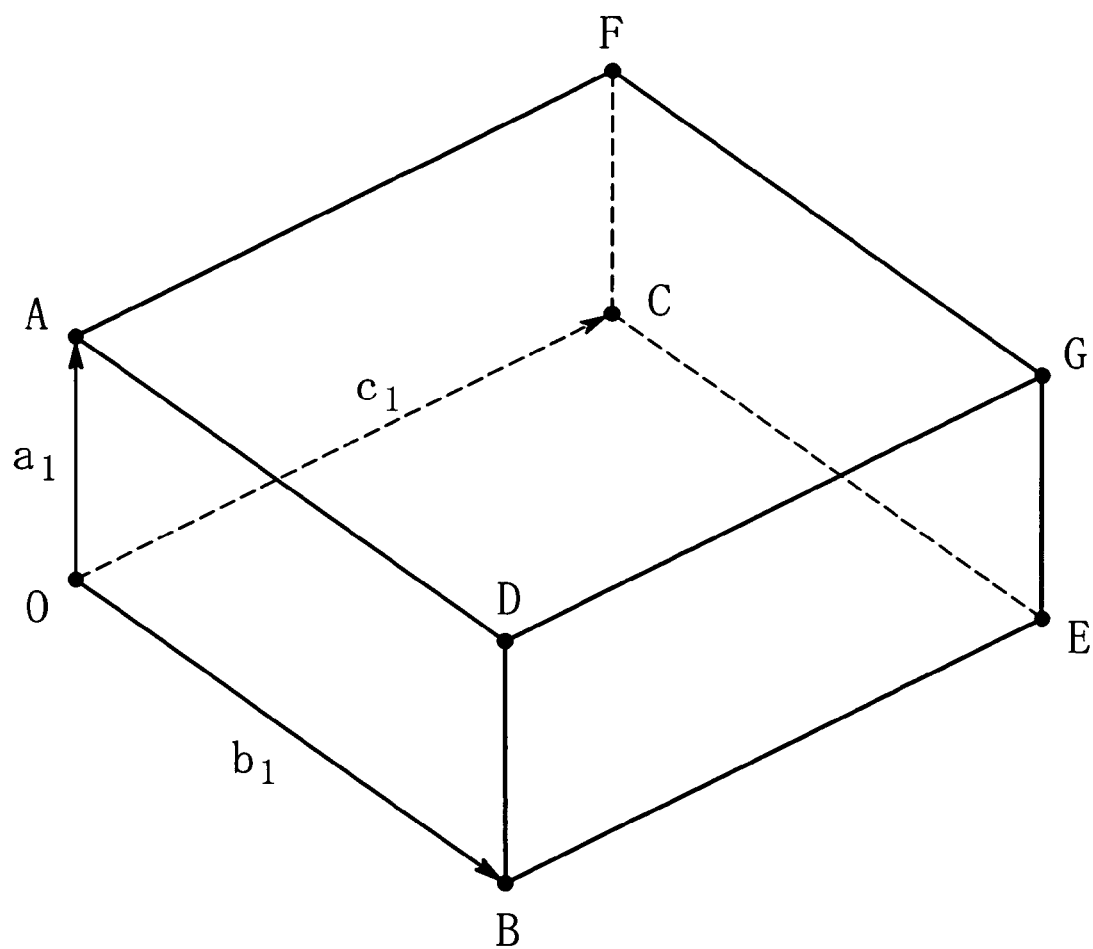
FIG. 2 shows a screen image displaying three-dimensionally the real-space unit lattice of a twin component 1.

FIG. 2 shows a screen image displaying three-dimensionally the real-space unit lattice of a twin component 1. The real-space unit lattice is defined as a parallelepiped made of real lattice vectors $a_1$, $b_1$ and $c_1$ which start at the origin O of the real space and extend along the respective crystal axes. The eight apexes of the unit lattice, i.e., points O and A through G, have respective coordinates which are expressed by equations (9) through (16) in FIG. 3 using the coordinates of equations (3) through (5) in FIG. 1. Thus, if the crystal orientation matrices of equation (1) in FIG. 1 are found, the coordinates of the real lattice vectors are determined as shown in equations (3) through (5) in FIG. 1, and further the coordinates of the apexes are determined as shown in equations (9) through (16) in FIG. 3, so that the real space unit lattice can be depicted as shown in FIG. 2.

A three-dimensional figure like FIG. 2 can be easily depicted with the use of any three-dimensional computer graphics software which is referred to as 3DCG hereinafter. Namely, when the above-described eight apex coordinates are input into the 3DCG, a three-dimensional figure like FIG. 2 is displayed. The 3DCG can execute operations of rotation, scaling up and down and translation of a depicted object which is a three-dimensional figure, and can display on a screen the resultant figure after such operations. Stating in detail, the eight apex coordinates are transformed with the use of a function of the rotational operation, a function of the scaling up and down operation or a function of the translational operation to create coordinates after such operations, and the resultant figure is displayed on a screen. An operator can order any operations of rotation, scaling up and down and translation with the use of input means attached to a computer, such as a keyboard, a mouse or a touch pad.

Similarly, the reciprocal-space primitive lattice is displayed in reciprocal space with the use of the coordinates of the reciprocal lattice vectors shown in equations (6) through (8) in FIG. 1. The reciprocal-space primitive lattice is defined as a parallelepiped made of reciprocal lattice vectors $a^*_1$, $b^*_1$ and $c^*_1$. The 3DCG can execute operations of rotation, scaling up and down and translation of the reciprocal-space primitive lattice too, and can display on a screen the resultant figure after such operations.

Next, there will be explained overlap of the diffraction spots between the twin components. According to the X-ray diffraction principle, one crystal lattice plane has one reflection index or Miller index (hkl) which corresponds to one reciprocal lattice point. Considering the reciprocal lattice point having a reflection index (hkl), the reciprocal lattice point coordinate $(x_i, y_i, z_i)$ of a twin component "i" is expressed by equation (17) in FIG. 4, noting that each of h, k and l of the reflection index is a positive integer, a negative integer or zero.

The degree of overlap of the diffraction spots may be determined with the following procedure. All of observable (i.e., satisfying the X-ray diffraction requirement) reciprocal lattice points are found for the respective twin components. The coordinates of the found reciprocal lattice points are calculated using equation (17). Considering different twin components "i" and "j", the distance between a reciprocal lattice point belonging to the twin component "i" and another reciprocal lattice point belonging to the other twin component "j" is defined as an inter-reciprocal-lattice-point distance $\Delta_{ij}$. The inter-reciprocal-lattice-point distance $\Delta_{ij}$ is calculated using equation (18) in FIG. 4 for all combinations of any one of the reciprocal lattice points belonging to the twin component "i" and any one of the reciprocal lattice points belonging to the other twin component "j". When the inter-reciprocal-lattice-point distance is smaller than the predetermined threshold, it is defined as that the two reciprocal lattice points overlap each other.

Next, there will be explained a method of finding out all of the observable reciprocal lattice points. The distance between the reciprocal origin and a certain reciprocal lattice point is given by equation (19) in FIG. 4. The observable reflection satisfies equation (20) in FIG. 4, which means that the distance $d^*_i$ of a reciprocal lattice point from the reciprocal origin is smaller than the predetermined value $d^*_{max}$ which is usually about 8/nm. On the other hand, the upper and lower limits of the reflection index (hkl) of the observable reciprocal lattice point are given by equations (21) through (23) in FIG. 4. Therefore, all of the reflection indices (hkl) satisfying equations (21) through (23) can be selected and their distances $d^*_i$ can be calculated using equation (19) to determine whether the calculated value satisfies equation (20). If satisfied, the reciprocal lattice point is determined to be observable and is added to the reflection list. Such an operation is carried out for all of the twin components to collect all of the observable reciprocal lattice points.

It is assumed that the number of the twin components is N, which is an integer not smaller than two, and the number of the observable reciprocal lattice points is $M_1$ for twin component 1, $M_2$ for twin component 2, ..., $M_n$ for twin component n, these number being obtained by the calculation described above. Only a combination of the reciprocal lattice points belonging to different twin components has a possibility of overlap. Then, the inter-reciprocal-lattice-point distance $\Delta_{ij}$ of equation (18) in FIG. 4 is calculated for all combinations of any one of $M_1$ reciprocal lattice points belonging to the twin component 1 and any one of $M_2$ reciprocal lattice points belonging to the twin component 2. If the distance $\Delta_{ij}$ is smaller than the threshold which is usually between 0.1/nm and 1/nm, the combination is determined as overlap and each of the two reciprocal lattice points is allowed to have a overlap flag which is a mark of overlap. Such an operation should be carried out for all combinations of different twin components, such as a combination of twin components 1 and 2, a combination of twin components 1 and 3, ..., and so on.

All of the reciprocal lattice points obtained by the above-described calculation are displayed using 3DCG on a screen of an image display device such as a CRT device, a liquid crystal display and an electroluminescent display. The reciprocal lattice point may be denoted, for example, by a sphere whose center is at the reciprocal lattice point on a screen. Other than the sphere, any shape may be used provided that its position can be ascertained, such as a dot, a parallelepiped, a star and so on. It is convenient for distinguishing twin components to display the reciprocal lattice points coming from different twin components with different colors. Operations of rotation, scaling up and down and translation of a picture image are important in displaying three-dimensionally the reciprocal lattice points in the reciprocal space. If the picture image is scaled down, all of the reciprocal lattice points causing X-ray diffraction can be observed to understand the total distribution of the reciprocal lattice points. If the picture image is rotated, the distribution of the reciprocal lattice points can be observed with various visual axes. If the picture image is scaled up, a certain desired region can be observed in a magnified form to look at the degree of overlap of the reciprocal lattice points. If the enlarged picture image is translated, the region which should be observed in a magnified form can be altered.

Next, there will be explained some examples of picture images according to the present invention with the use of an actual twinned crystal sample. The actual sample consisting of two twin components was analyzed with the use of X-ray single crystal structure analytical equipment and two crystal orientation matrices were found as shown in equations (24) and (25) in FIG. 5. An interrelation matrix R between the twin components was found as shown in equation (26) in FIG. 5 based on the two crystal orientation matrices. The interrelation matrix R may also be referred to as the twin law and is a rotation matrix expressing the interrelationship between the two crystal orientation matrices. Analyzing the interrelation matrix R gives the following information. The two twin components have a common a-axis of real lattice and have a special relationship in that when one twin component is rotated around a-axis by 179.984 degrees, it coincides with the other twin component. It can be understood with the information that the two twin components have the special relationship in that they will overlap each other when one component is rotated by 180 degrees relative to the other component. It should be noted that the knowledge about crystallography would be necessary to obtain such information by analyzing the interrelation matrix R. With the present invention, however, the relationship between the two twin components can be easily understood three-dimensionally on a screen without the knowledge about crystallography, as will be described below.

Figure 6:
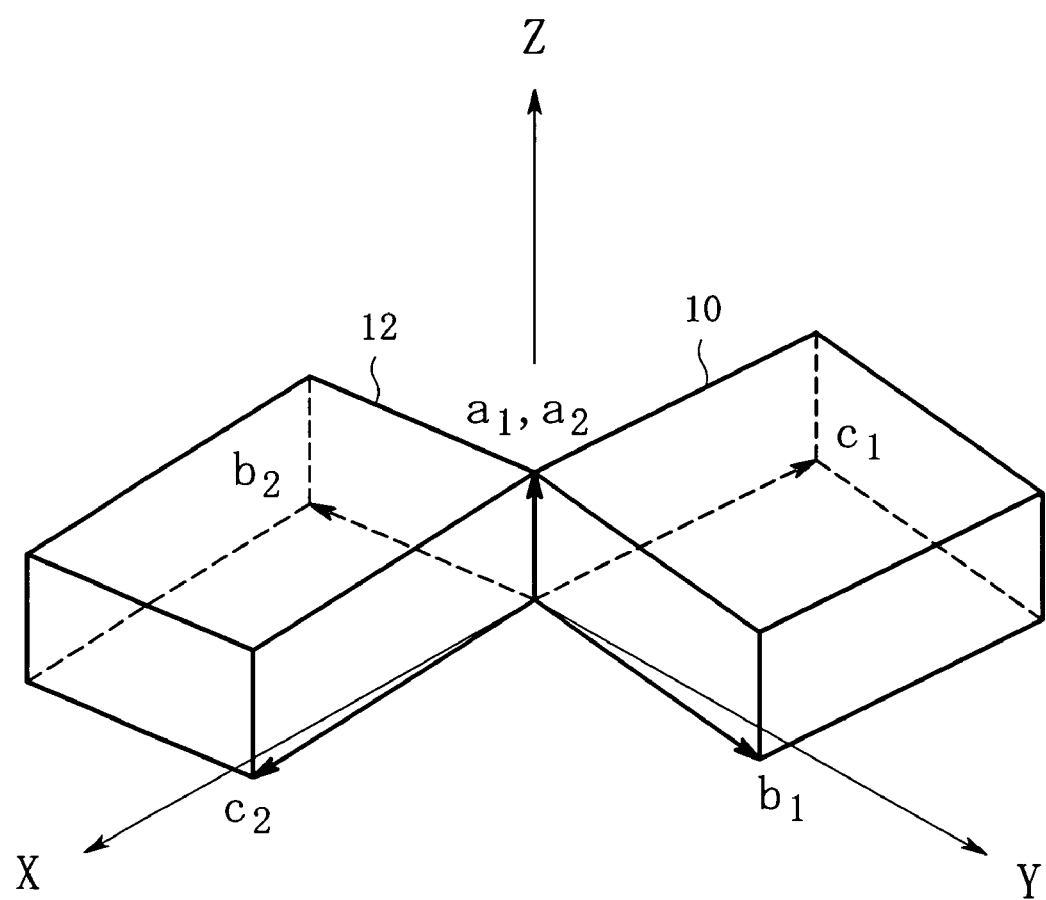
FIG. 6 shows a screen image displaying three-dimensionally the real-space unit lattices of the two twin components in three-dimensional real space.

FIG. 6 shows a screen image displaying three-dimensionally the real-space unit lattices of the two twin components on a screen expressing three-dimensional real space. The real lattice vectors of the twin component 1 are $a_1$, $b_1$ and $c_1$ and the real-space unit lattice 10 of the twin component 1 is expressed by a parallelepiped made of these vectors. The real lattice vectors of the twin component 2 are $a_2$, $b_2$ and $c_2$ and the real-space unit lattice 12 of the twin component 2 is expressed by another parallelepiped made of these vectors. The real lattice vectors $a_1$ and $a_2$ of the two twin components overlap each other. The coordinate system of the real space is XYZ coordinate system. The vectors $a_1$ and $a_2$ are arranged so as to coincide with Z-axis. It would be easily surmised that when the real-space unit lattice 10 of the twin component 1 is rotated by 180 degrees around Z-axis, it would coincide with the real-space unit lattice 12 of the twin component 2.

Figure 22:
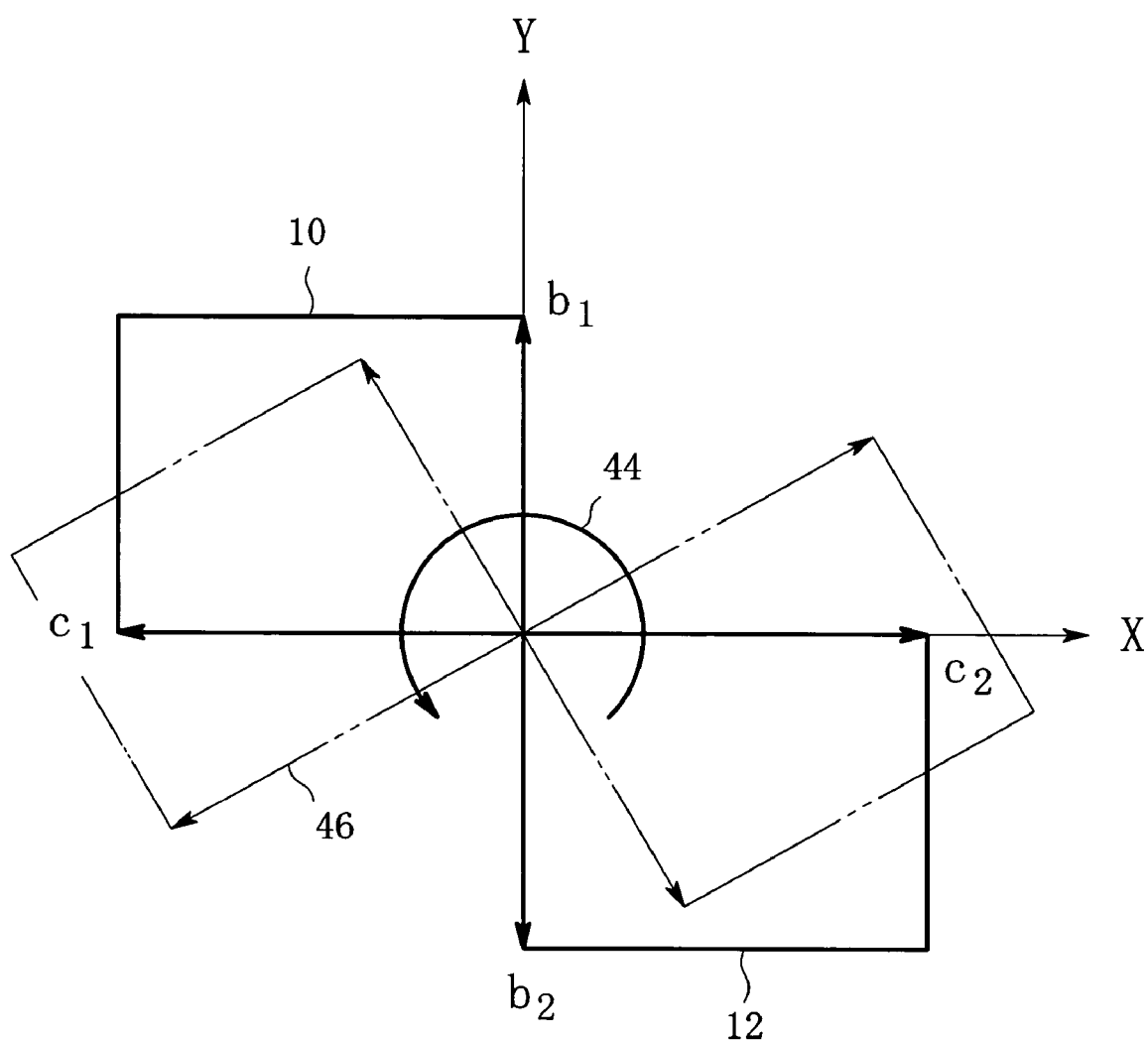
FIG. 22 is a plan view of the real-space unit lattices shown in FIG. 6 as viewed from a Z-direction.
Figure 23:
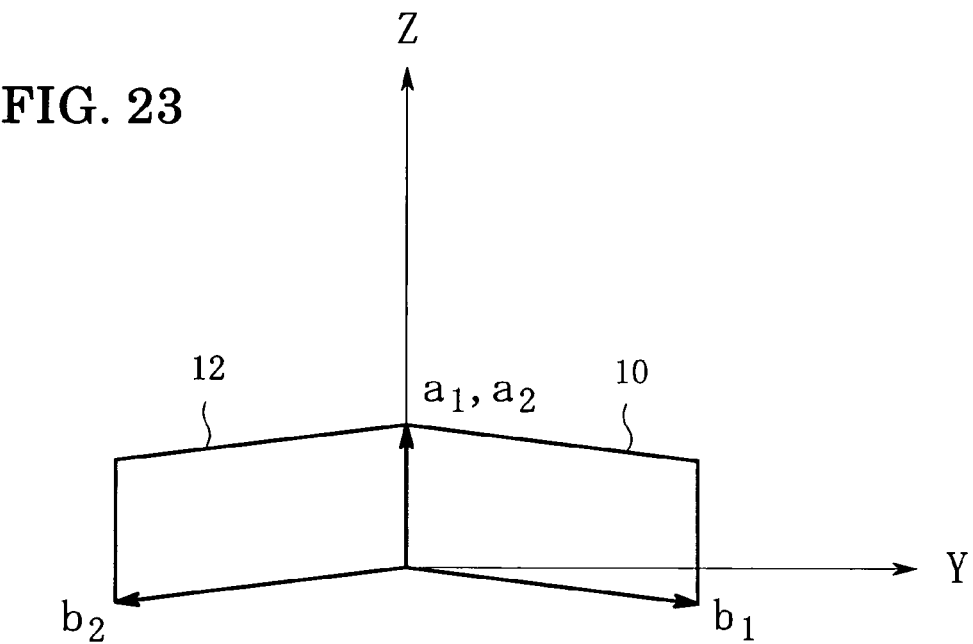
FIG. 23 is a front view of the real-space unit lattices shown in FIG. 6 as viewed from an X-direction.
Figure 24:
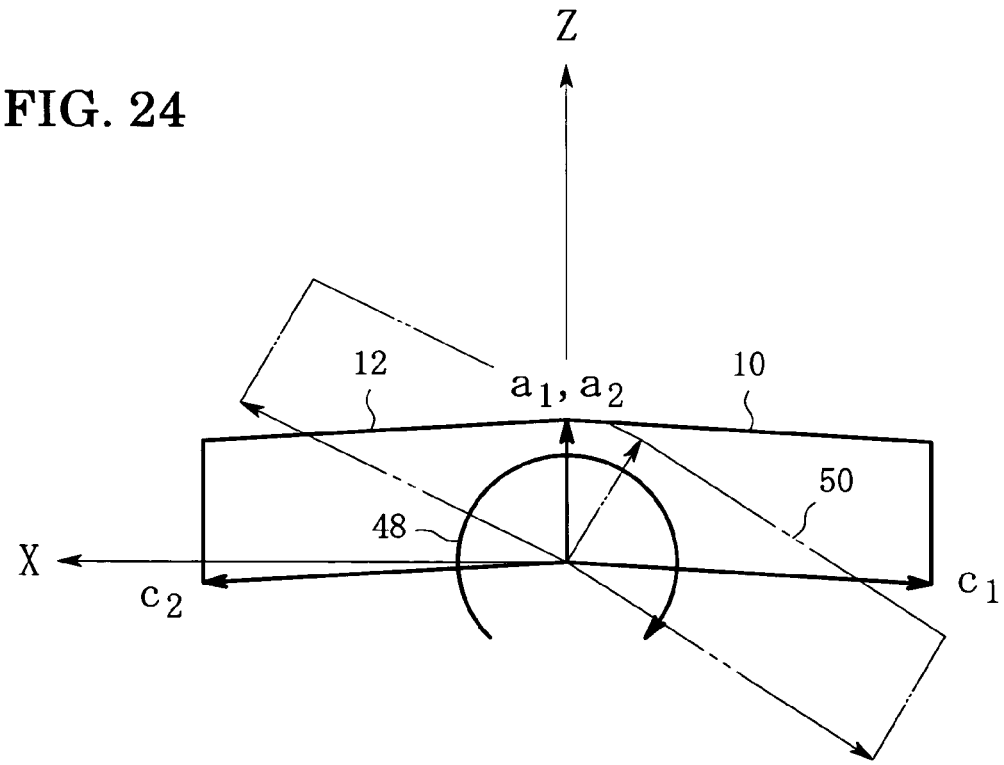
FIG. 24 is a side view of the real-space unit lattices shown in FIG. 6 as viewed from a Y-direction.

FIG. 22 is a plan view of the real-space unit lattices shown in FIG. 6 as viewed from a Z-direction. FIG. 23 is a front view of the real-space unit lattices shown in FIG. 6 as viewed from an X-direction. FIG. 24 is a side view of the real-space unit lattices shown in FIG. 6 as viewed from a Y-direction.

Figure 7:
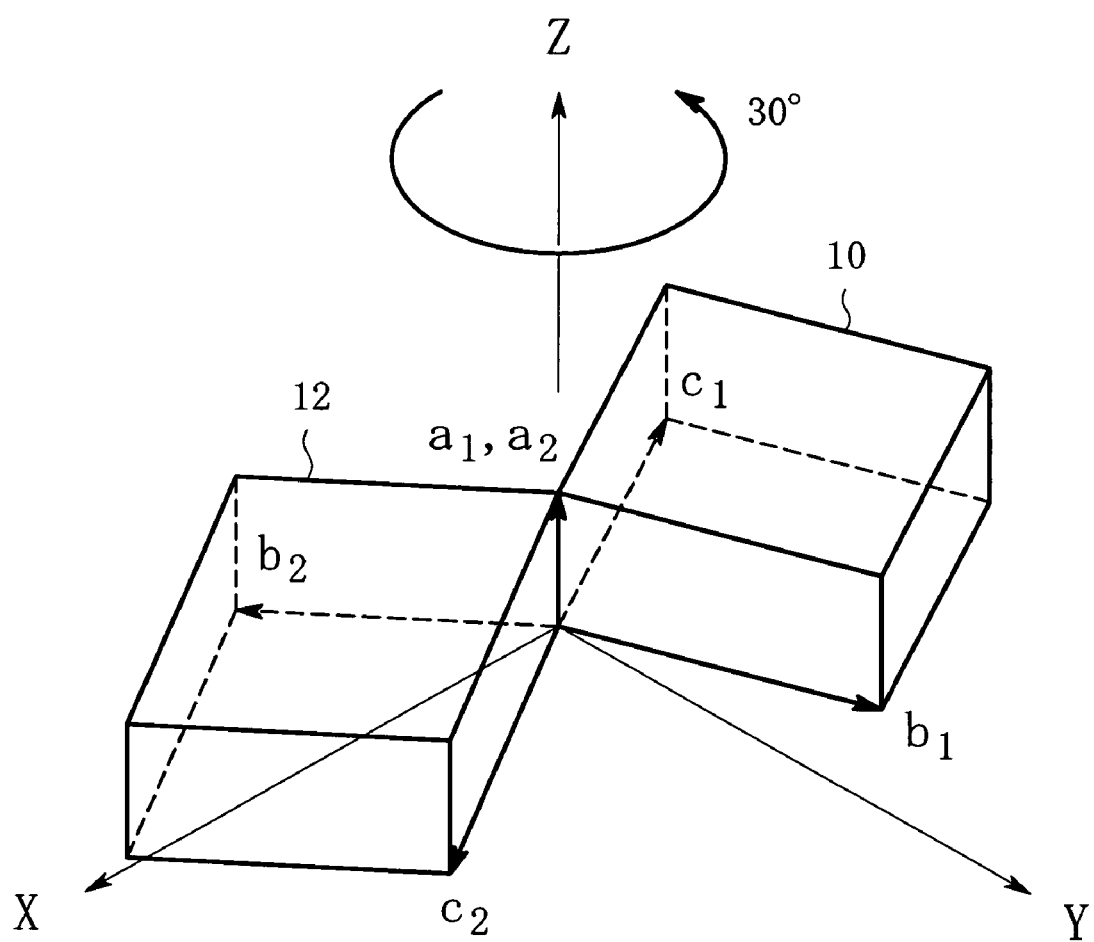
FIG. 7 shows a screen image in which the picture objects in FIG. 6 have been rotated by 30 degrees around Z-axis.
Figure 8:
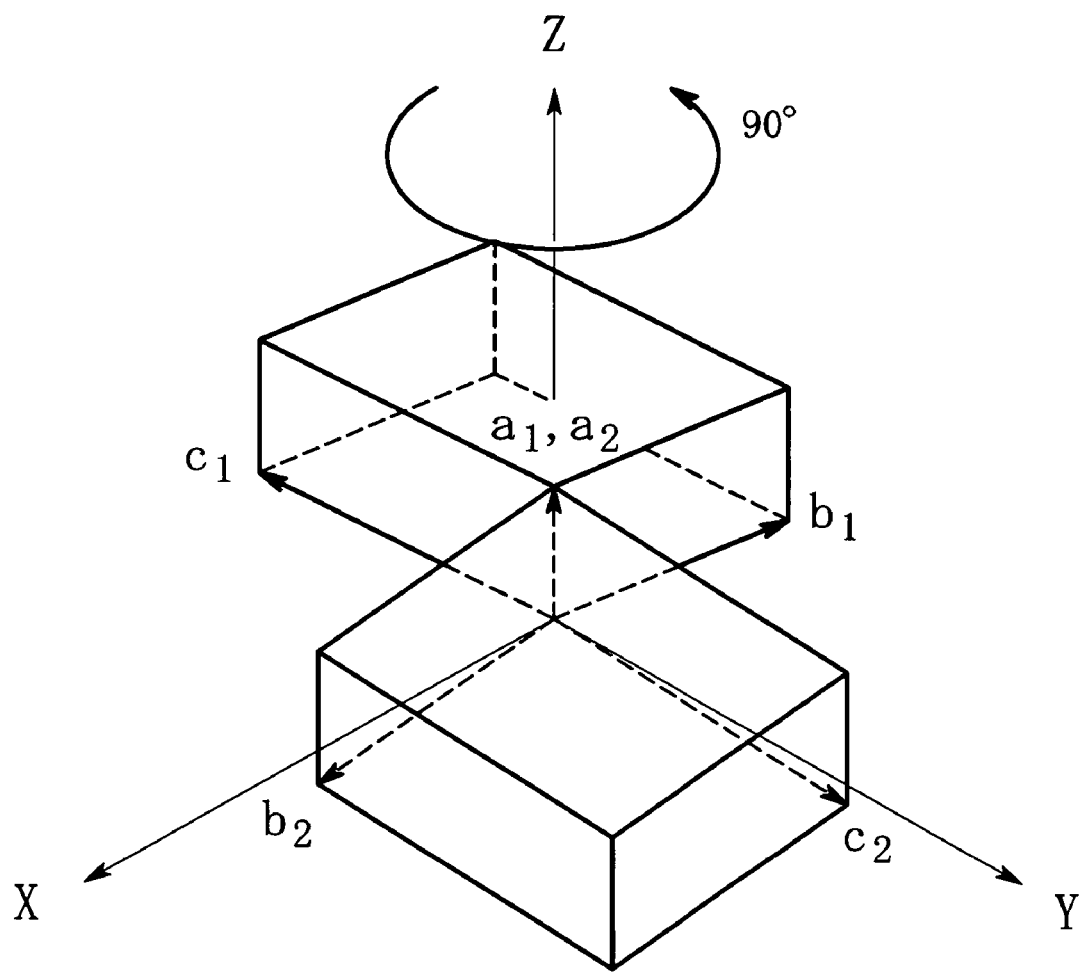
FIG. 8 shows a screen image in which the picture objects in FIG. 6 have been rotated by 90 degrees around Z-axis.
Figure 9:
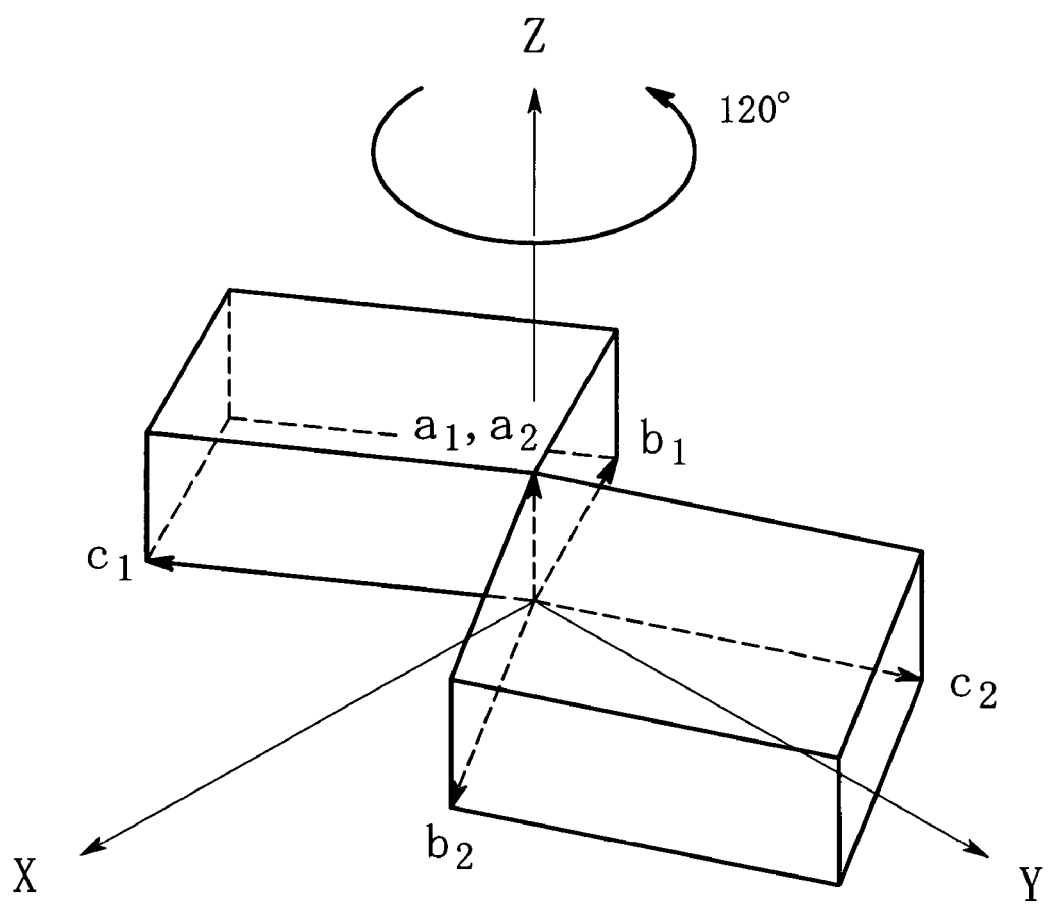
FIG. 9 shows a screen image in which the picture objects in FIG. 6 have been rotated by 120 degrees around Z-axis.
Figure 10:
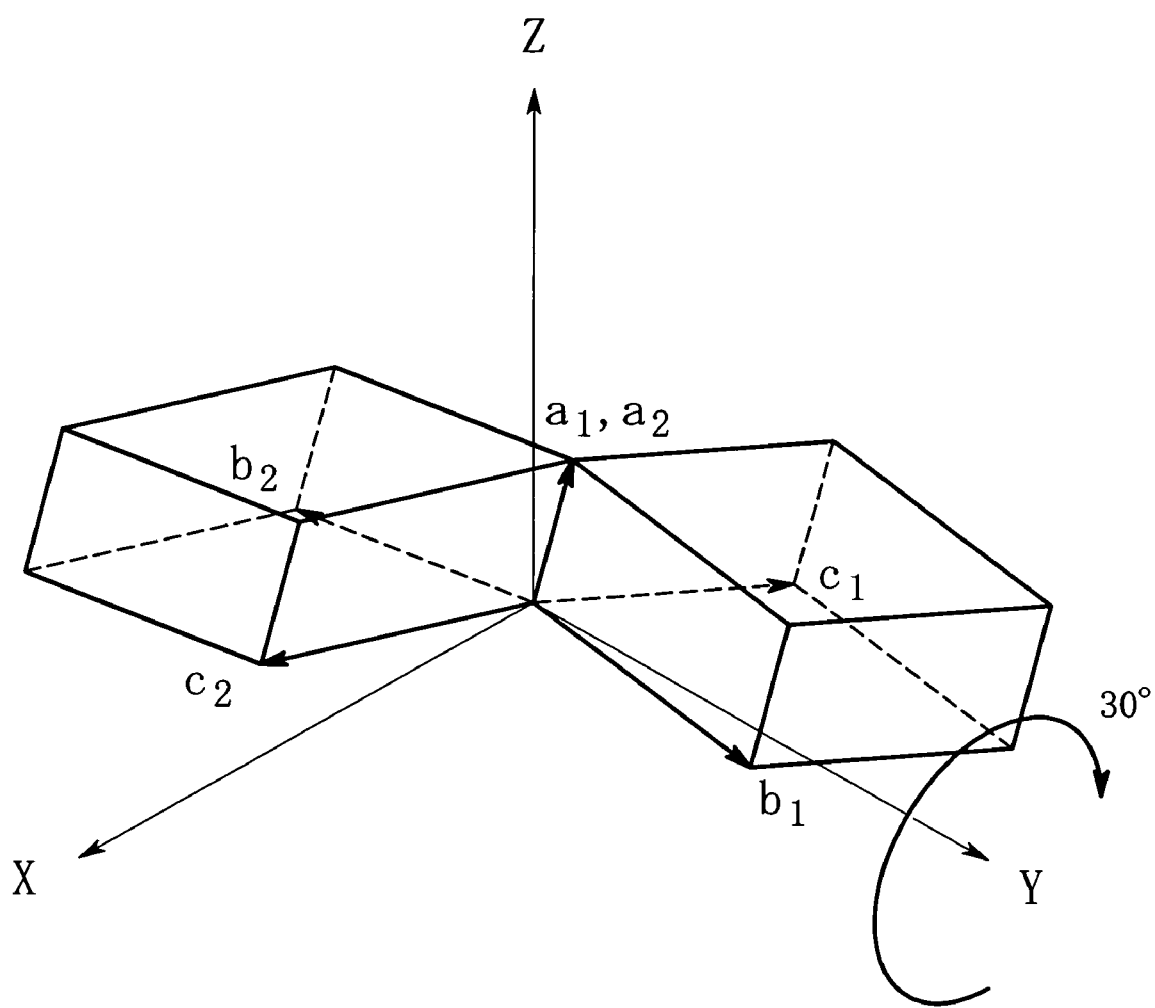
FIG. 10 shows a screen image in which the picture objects in FIG. 6 have been rotated by 30 degrees around Y-axis.
Figure 11:
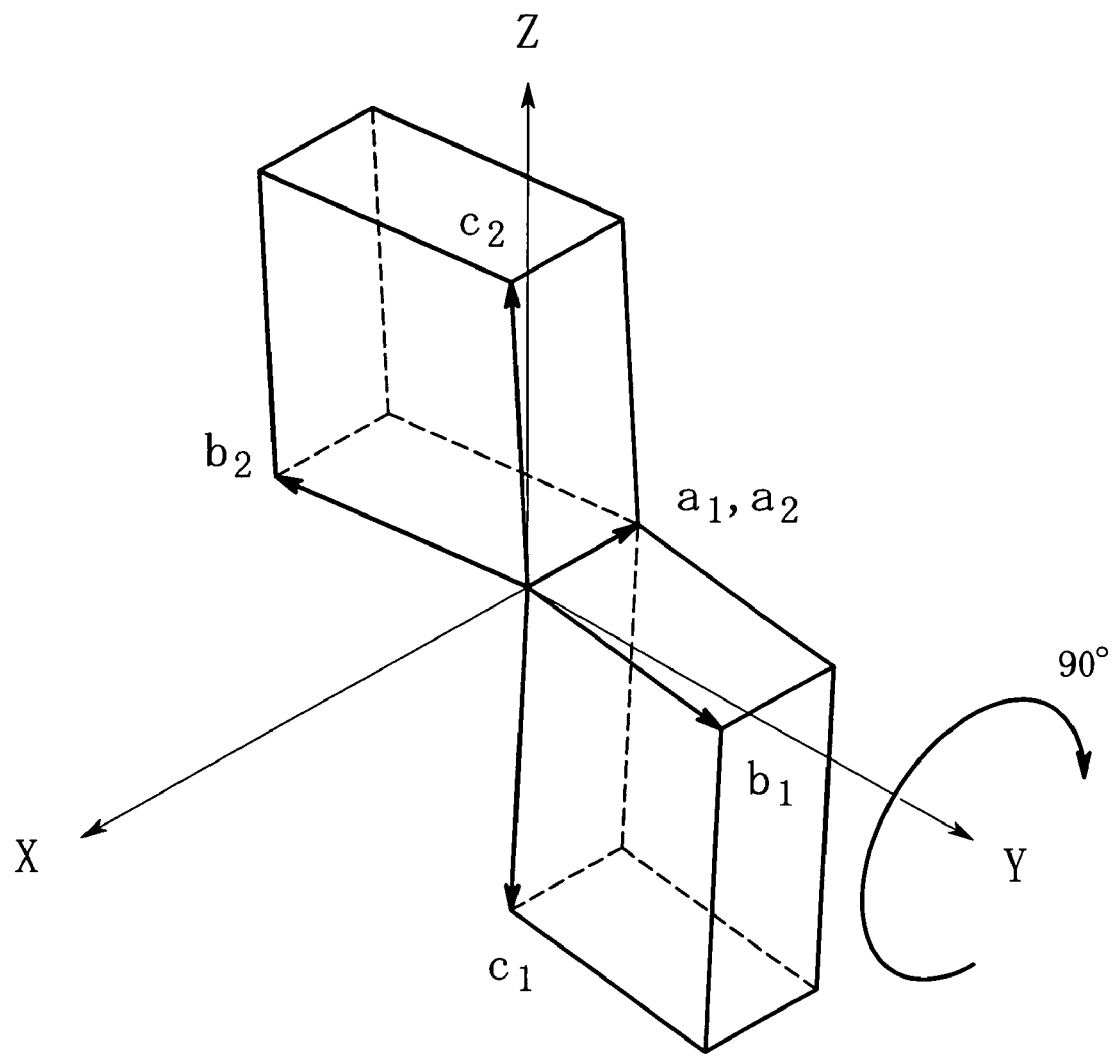
FIG. 11 shows a screen image in which the picture objects in FIG. 6 have been rotated by 90 degrees around Y-axis.

FIG. 7 shows a screen image in which the picture objects in FIG. 6 (i.e., the real-space unit lattice 10 of the twin component 1 and the real-space unit lattice 12 of the twin component 2) have been rotated by 30 degrees around Z-axis counterclockwise as viewed from the positive side of Z-axis, noting that the coordinate axes XYZ remain as they are and only the picture objects have been rotated. This means that the picture objects are observed three-dimensionally with another visual axis different from that in FIG. 6. FIG. 22 shows this 30-degree rotation 44 around Z-axis and the resultant real-space unit lattices 46 after the rotation. FIG. 8 shows a screen image in which the picture objects in FIG. 6 have been rotated by 90 degrees counterclockwise around Z-axis. FIG. 9 shows a screen image in which the picture objects in FIG. 6 have been rotated by 120 degrees counterclockwise around Z-axis. FIG. 10 shows a screen image in which the picture objects in FIG. 6 have been rotated by 30 degrees around Y-axis clockwise as viewed from the positive side of Y-axis. FIG. 24 shows this 30-degree rotation 48 around Y-axis and the resultant real-space unit lattices 50 after the rotation. FIG. 11 shows a screen image in which the picture objects in FIG. 6 have been rotated by 90 degrees clockwise around Y-axis. As shown in FIGS. 6 through 11, the real-space unit lattices can be observed three-dimensionally with various visual axes, so that the relationship between the two twin components can be easily understood.

In displaying the real-space unit lattices in FIGS. 6 through 11, it is preferable to display the twin components 1 and 2 with different colors.

Figure 12:
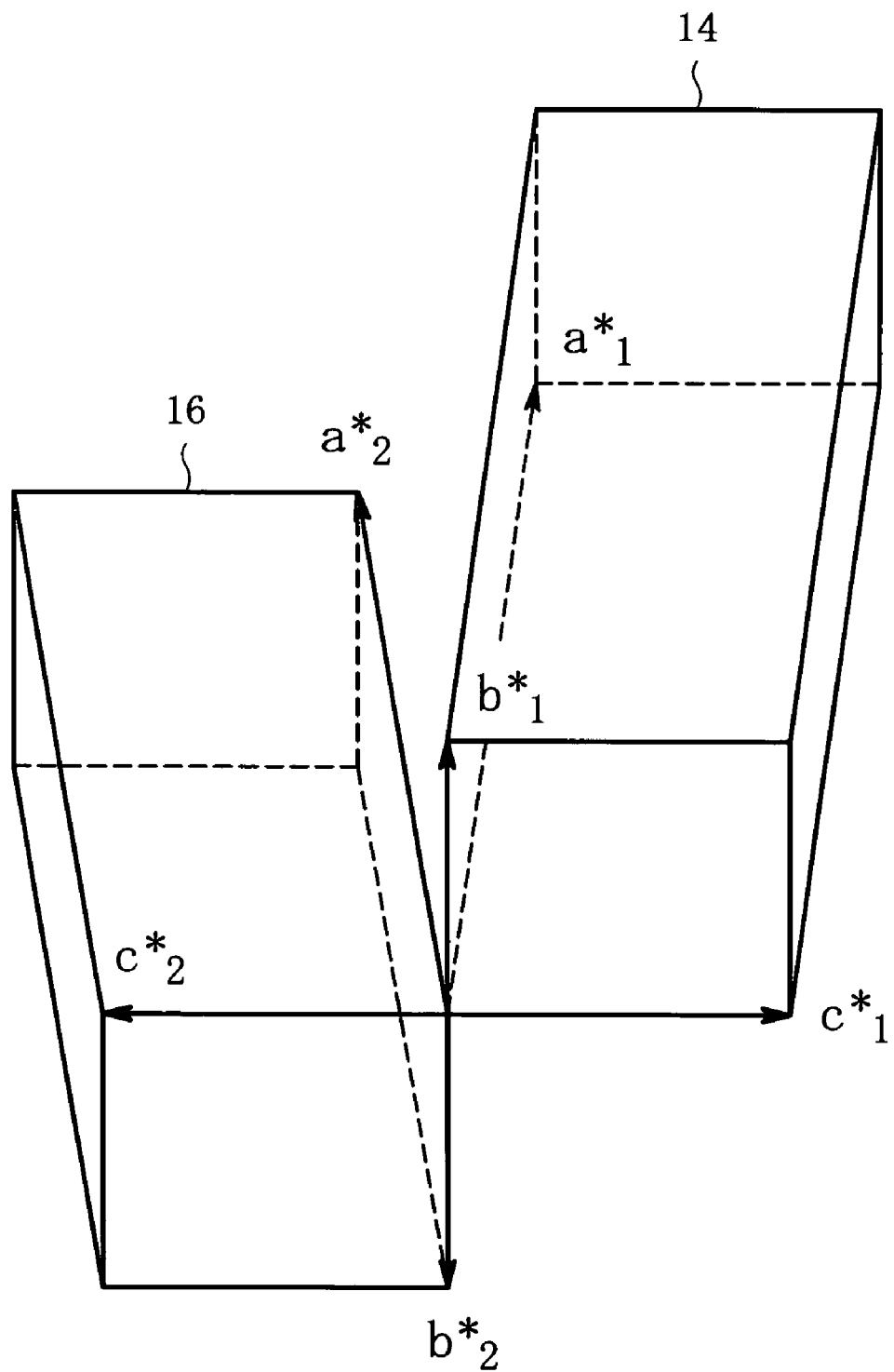
FIG. 12 shows a screen image displaying three-dimensionally the reciprocal-space primitive lattices of the two twin components in three-dimensional reciprocal space.

FIG. 12 shows a screen image displaying three-dimensionally the reciprocal-space primitive lattices of the two twin components on a screen expressing three-dimensional reciprocal space. The reciprocal lattice vectors of the twin component 1 are $a^*_1$, $b^*_1$ and $c^*_1$ and the reciprocal-space primitive lattice 14 of the twin component 1 is expressed by a parallelepiped made of these vectors. The reciprocal lattice vectors of the twin component 2 are $a^*_2$, $b^*_2$ and $c^*_2$ and the reciprocal-space primitive lattice 16 of the twin component 2 is expressed by a parallelepiped made of these vectors. The following matters can be seen from this picture image: (1)

b*₁-c*₁ plane (i.e., a plane including b*₁-axis and c*₁-axis) and b*₂-c*₂ plane are on the same plane; (2) b*₁-axis and b*₂-axis are on the same straight line and extends in the opposite directions; and (3) c*₁-axis and c*₂-axis are on the same straight line and extends in the opposite directions. It would be surmised with this information that, in a plane having the reflection index h=0, the reciprocal lattice points having the reflection index (0 kl) of the twin component 1 and the reciprocal lattice points having the reflection index (0,−k,−l) of the twin component 2 almost perfectly overlap each other.

The reciprocal-space primitive lattices shown in FIG. 12 may also be rotated around various axes to be displayed after rotation, similarly as in the case of the real-space unit lattices shown in FIGS. 6 through 12, so that there can be easily obtained useful information in determining the relationship between the two twin components, especially the degree of overlap of the reciprocal lattice points it is preferable for also the reciprocal-space primitive lattices to display the twin components 1 and 2 with different colors.

Figure 13:
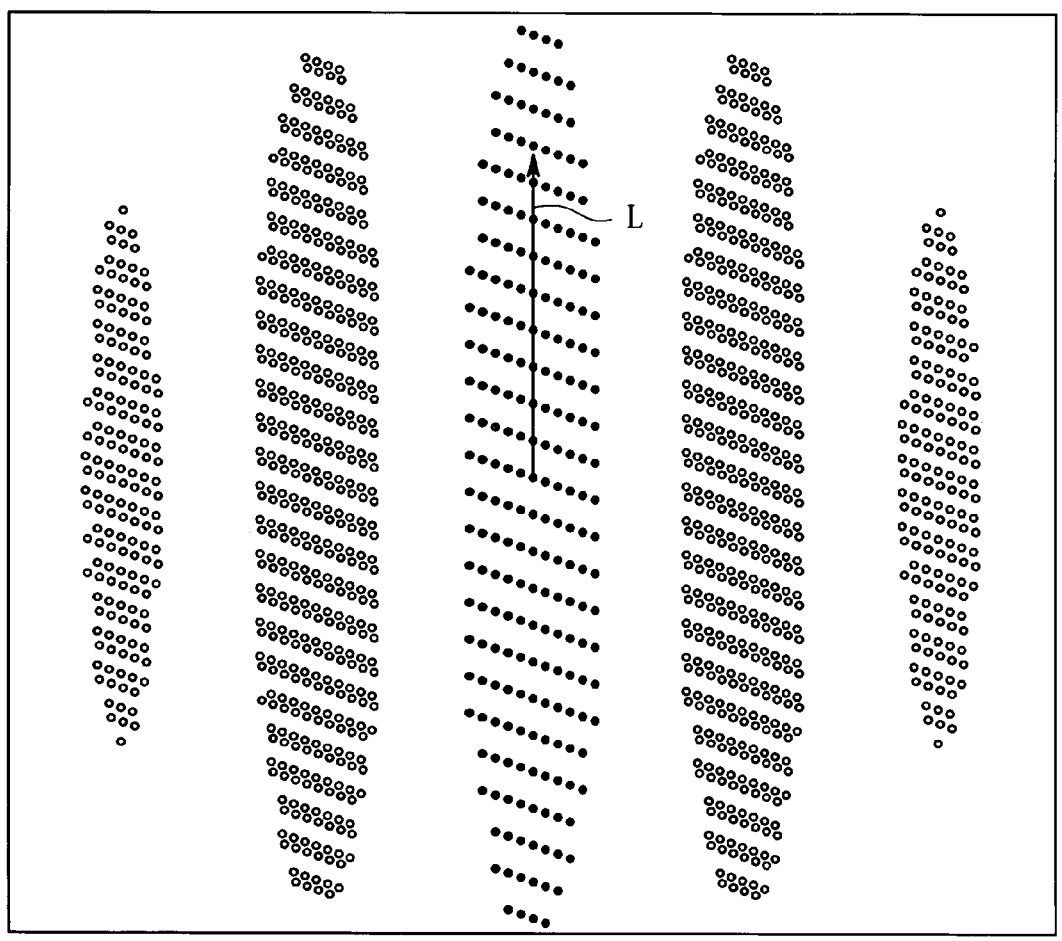
FIG. 13 shows a screen image displaying reciprocal lattice points causing X-ray diffraction with a distinction between the twin components in the three-dimensional reciprocal space.

FIG. 13 shows a screen image displaying reciprocal lattice points causing X-ray diffraction with a distinction between the twin components on a screen expressing the three-dimensional reciprocal space. The center of the screen is positioned at the origin of the reciprocal space, that is, (hkl)=(000). L-axis extends vertically on the screen and H-axis and K-axis reside in a plane perpendicular to L-axis.

Figure 14:
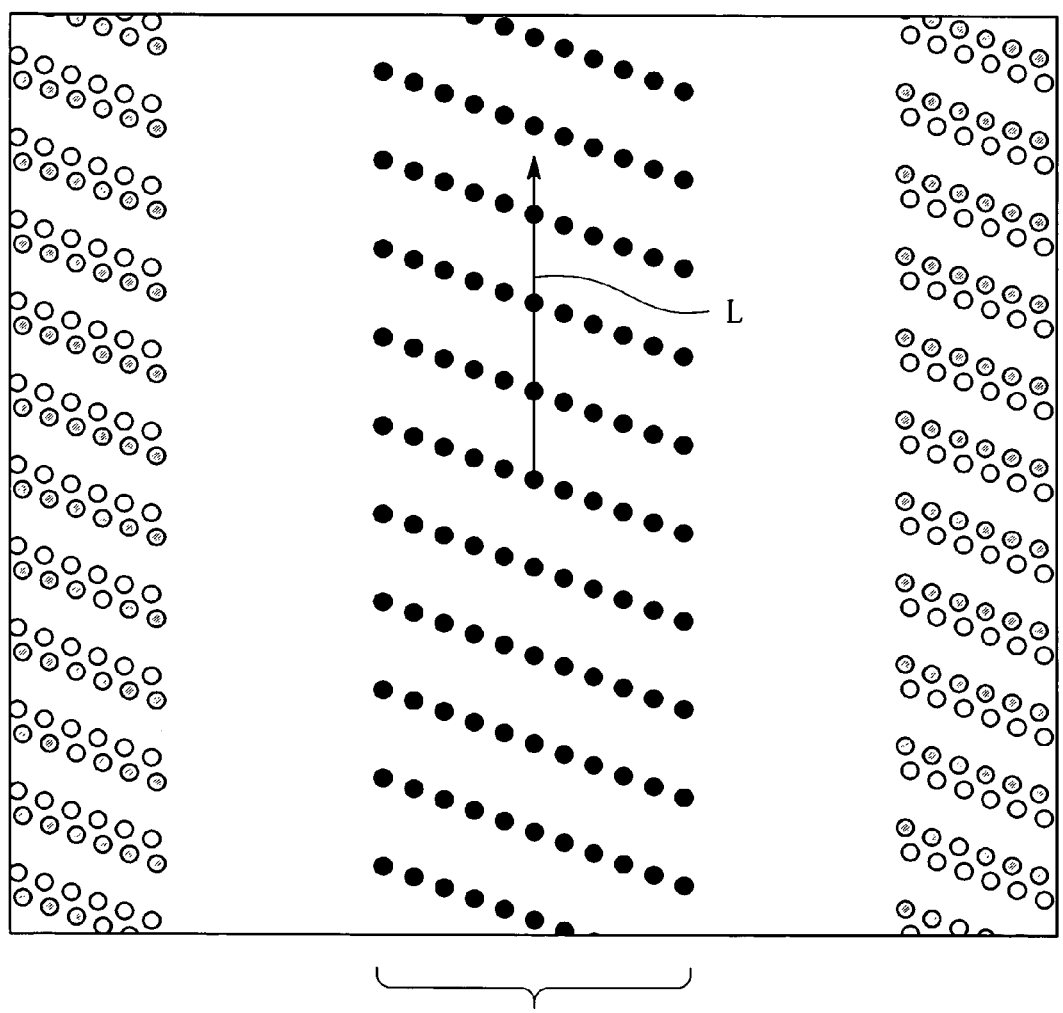
FIG. 14 shows a screen image displaying three-dimensionally in a magnified form the reciprocal lattice points near the origin of the reciprocal space among the reciprocal lattice points shown in FIG. 13.

FIG. 14 shows a screen image displaying three-dimensionally in a magnified form the reciprocal lattice points near the origin of the reciprocal space among the reciprocal lattice points shown in FIG. 13. Each of the reciprocal lattice points coming from the twin component 1 is denoted by a circle with hatching, while each of the reciprocal lattice points coming from the twin component 2 is denoted by a white circle. Each of the overlapped reciprocal lattice points of twin components 1 and 2 is denoted by a black circle. It should be noted that, in an actual screen image, these three kinds of the reciprocal lattice points are displayed with different colors, such as green for twin component 1, orange for twin component 2 and blue for overlapped.

According to having been surmised from the picture of the reciprocal-space primitive lattices shown in FIG. 12, the reciprocal lattice points 18 in FIG. 14 residing on the reciprocal lattice plane (0 kl), which are denoted by black circles, are in the overlapped condition between the reciprocal lattice points of the twin component 1 and the reciprocal lattice points of the twin component 2.

Figure 15:
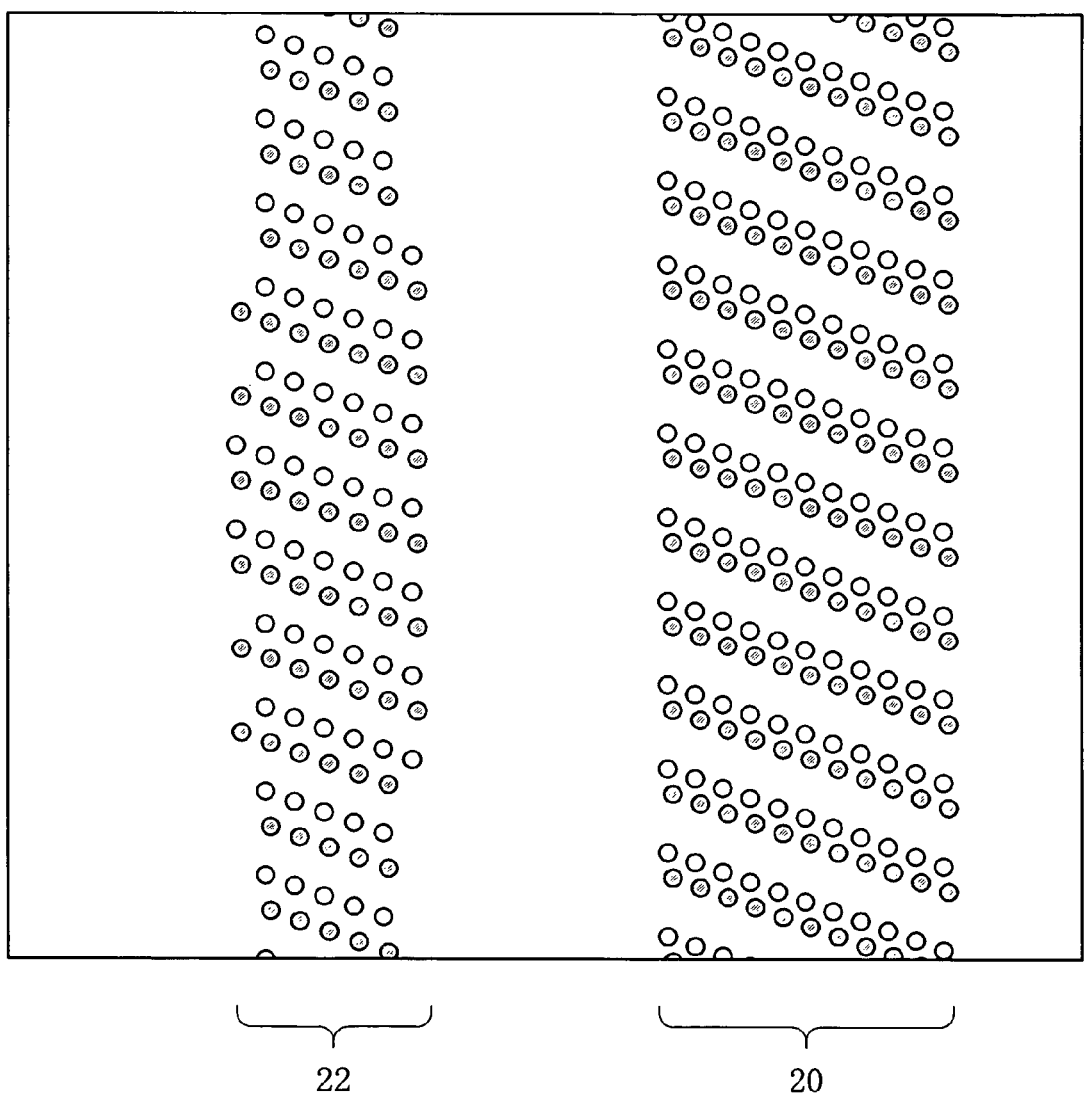
FIG. 15 shows a screen image displaying three-dimensionally in a magnified form the reciprocal lattice points belonging to the reciprocal lattice planes (1 kl) and (2 kl)

FIG. 15 shows a screen image displaying three-dimensionally in a magnified form the reciprocal lattice points 20 belonging to the reciprocal lattice planes (1 kl) and the reciprocal lattice points 22 belonging to the reciprocal lattice planes (2 kl). This picture image is derived by translating the reciprocal lattice points shown in FIG. 14 in a plane perpendicular to L-axis, so that other reciprocal lattice points in another region of the reciprocal space can be displayed. Similarly as in FIG. 14, each of the reciprocal lattice points coming from the twin component 1 is denoted by a circle with hatching, while each of the reciprocal lattice points coming from the twin component 2 is denoted by a white circle. Displaying in a magnified form makes it easy to observe the degree of overlap of the reciprocal lattice points coming from the two twin components. If the reciprocal lattice points coming from the different components are close to each other, it is surmised that the diffraction lines would overlap each other.

Figure 16:
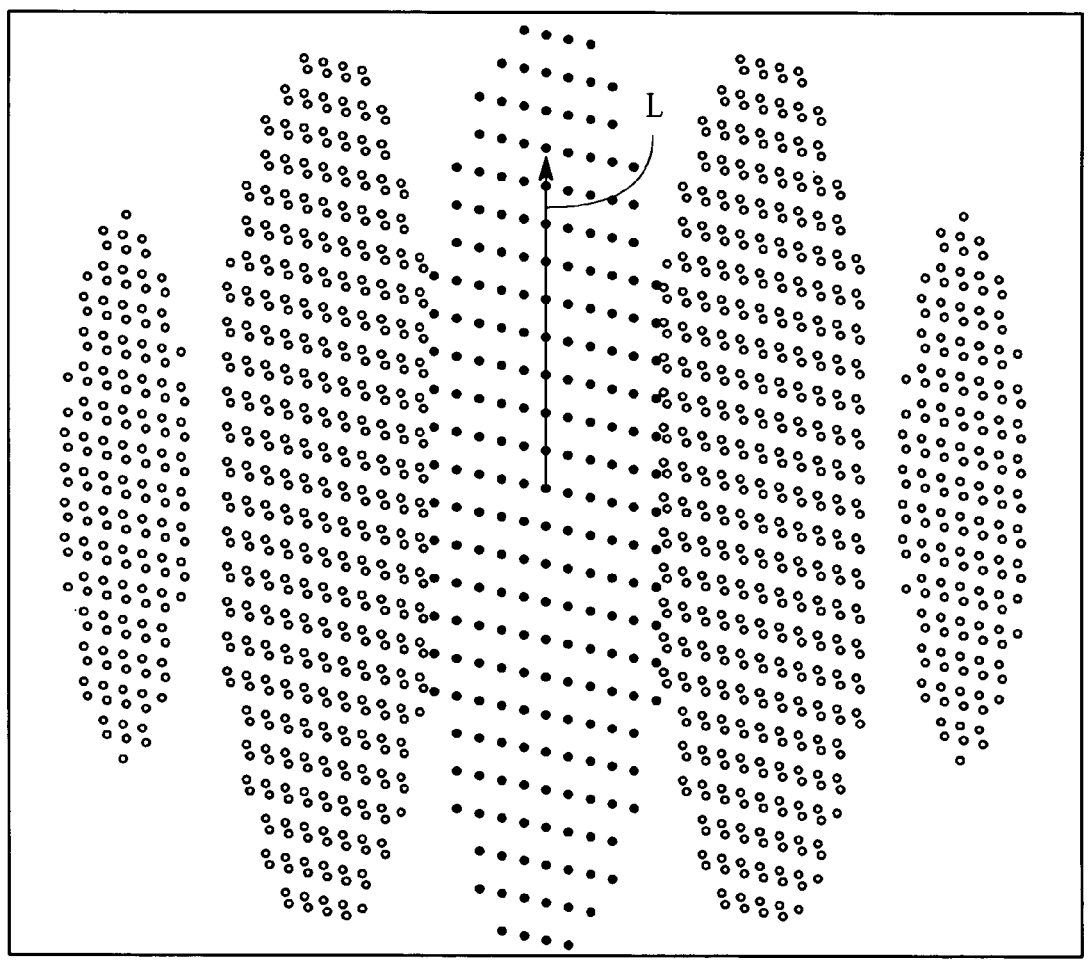
FIG. 16 shows a screen image in which the image of the reciprocal lattice points shown in FIG. 13 has been rotated by a certain angle around L-axis.
Figure 17A:
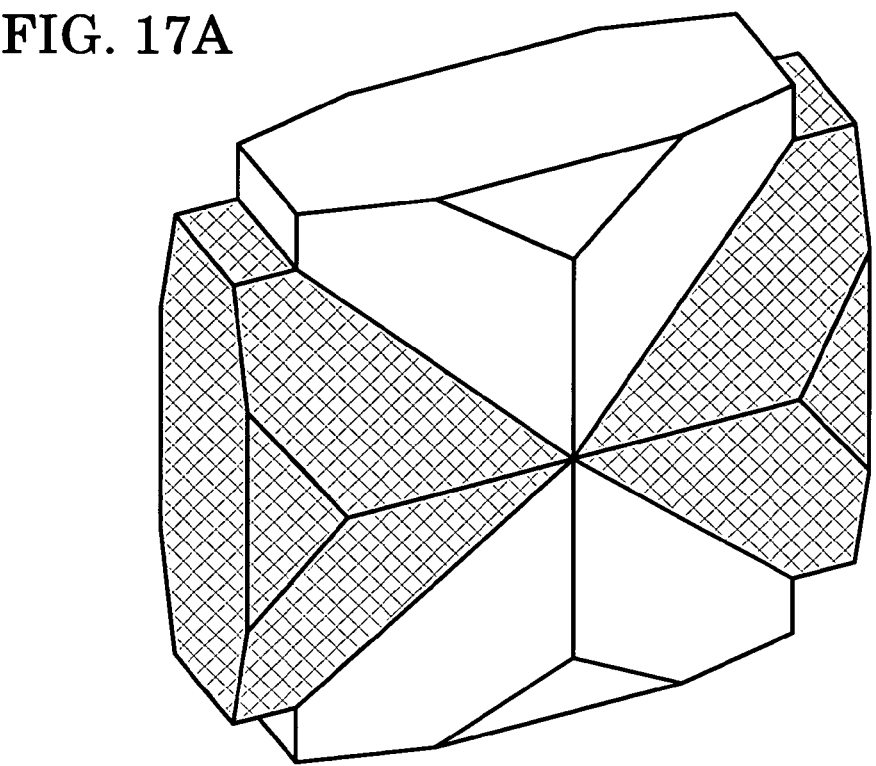
FIGS. 17A and 17B are perspective views of the twinned crystals.
Figure 17B:
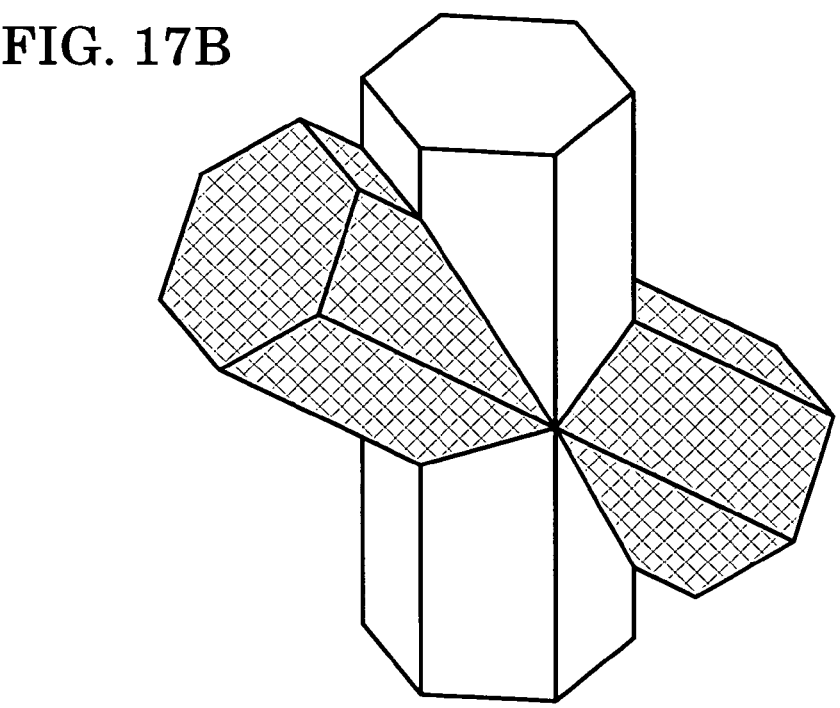
Figure 18A:
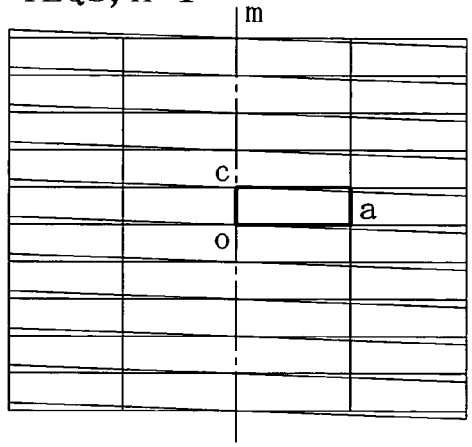
FIGS. 18A, 18B, 18C and 18D show prior art expressions displaying two-dimensionally two nets of the reciprocal lattice points coming from two twin components, the two nets overlapping each other.
Figure 18B:
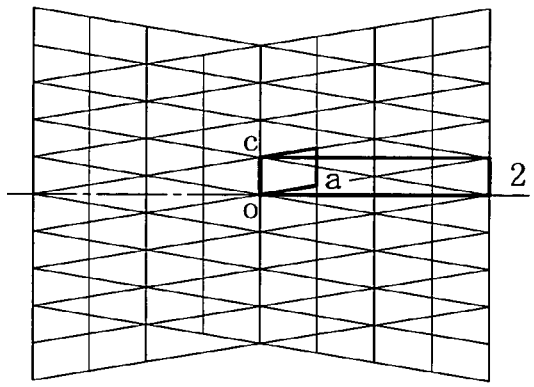
Figure 18C:
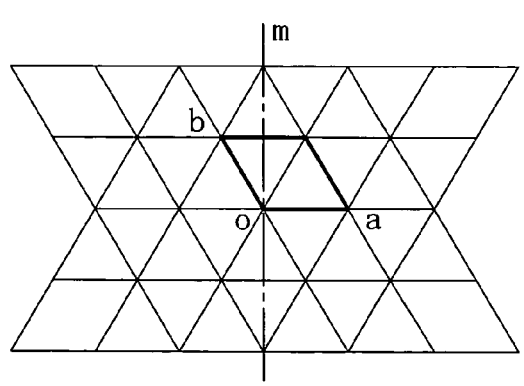
Figure 18D:
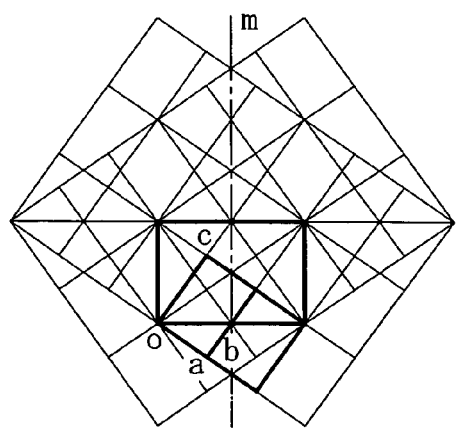
Figure 19:
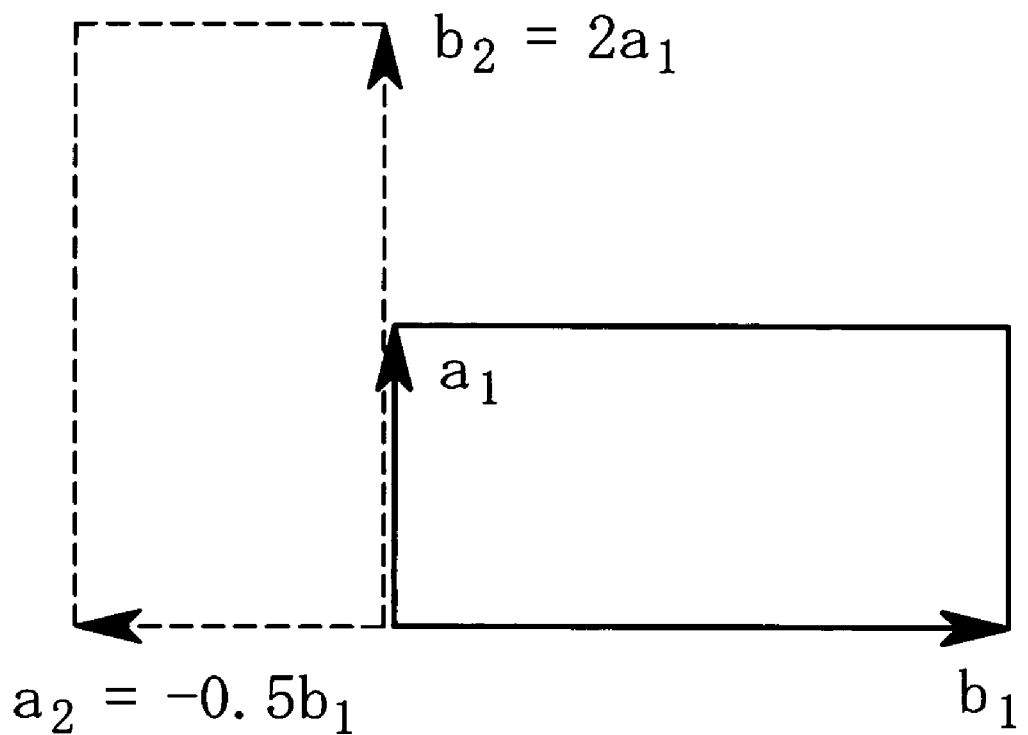
FIG. 19 shows a prior art expression displaying two-dimensionally the respective real-space unit lattice of two twin components on a two-dimensional plane.
Figure 20:
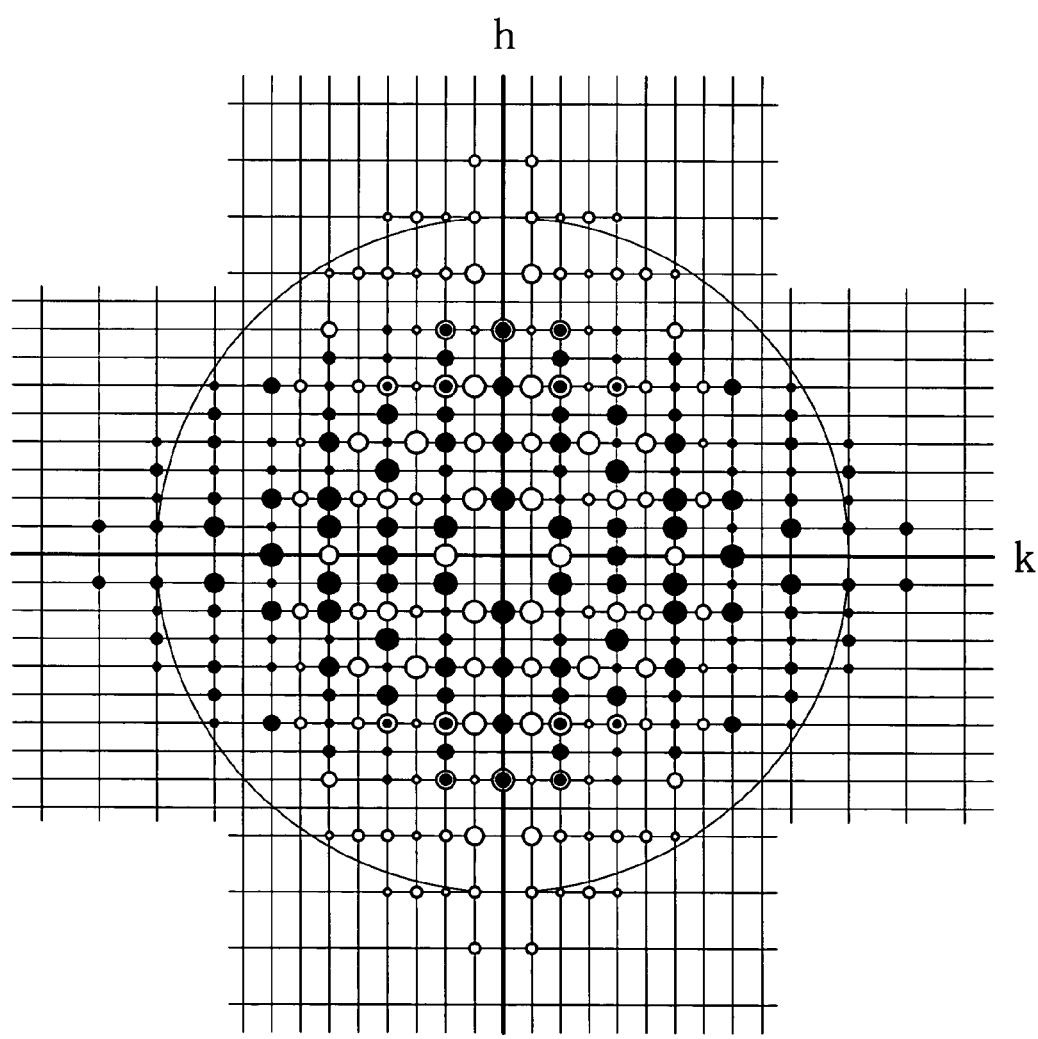
FIG. 20 shows a prior art expression displaying X-ray diffraction spots corresponding to the real-space unit lattices shown in FIG. 19 on a two-dimensional reciprocal lattice plane.

FIG. 16 shows a screen image in which the image of the reciprocal lattice points shown in FIG. 13 has been rotated by a certain angle around L-axis. The rotational operation allows the appearance of the reciprocal lattice points to be altered and makes it easy to understand the distribution of the reciprocal lattice points.

Figure 21:
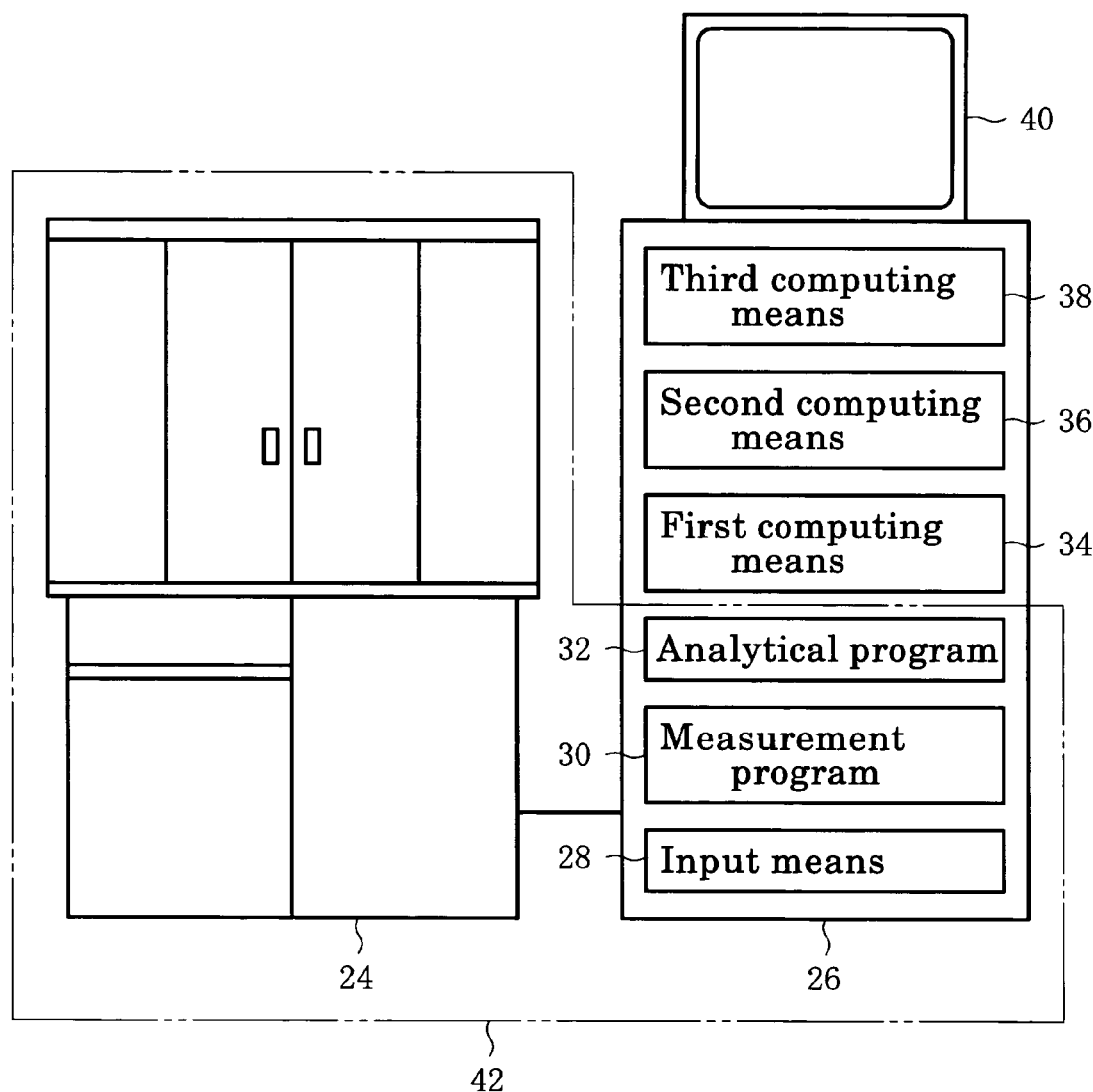
FIG. 21 shows a configuration of a twinned crystal analytical apparatus according the present invention.

FIG. 21 shows a configuration of a twinned crystal analytical apparatus according to the present invention. The twinned crystal analytical apparatus consists of: X-ray diffraction equipment 24 prepared as the hardware including the measurement optical system for X-ray single crystal structural analysis; and a console 26 taking charge of control and analysis. The console 26 includes: input means 28 for inputting measurement conditions and for giving operational commands; a measurement program 30 for executing automatically X-ray diffraction measurement; an analytical program 32 for analyzing the measurement result; the first computing means 34; the second computing means 36; the third computing means 38; and a display 40. The X-ray single crystal structure analytical equipment 42 in the present invention is comprised of the X-ray diffraction equipment 24 as the hardware and the input means 28, the measurement program 30 and the analytical program 32 in the console 26. The twinned crystal analytical apparatus according to the present invention is comprised of this X-ray single crystal structure analytical equipment 42, the three kinds of the computing means 34, 36 and 38 and the display 40.

The analytical program 32 finds the respective crystal orientation matrices of the twin components based on the measurement result. The first computing means 34 creates display data for displaying three-dimensionally the respective real-space unit lattices of plural twin components based on the crystal orientation matrices. FIGS. 6 through 11 show screen images of the display data which have been created by the first computing means 34. The second computing means 36 creates display data for displaying three-dimensionally the respective reciprocal-space primitive lattices of plural twin components based on the crystal orientation matrices. FIG. 12 shows a screen image of the display data which have been created by the second computing means 36. The third computing means 38 creates display data for displaying three-dimensionally the respective reciprocal lattice points, causing X-ray diffraction, of plural twin components. FIGS. 13 through 16 show screen images of the display data which have been created by the third computing means 38. The three computing means 34, 36 and 38 may be realized actually as respective functional blocks in the same computer software. The display data may be displayed in a display 40 such as a CRT device or a liquid crystal display.

What is claimed is:

1. An apparatus for analyzing a twinned crystal comprising:
   (a) X-ray single crystal structure analytical equipment which can obtain respective crystal orientation matrices of plural components of the twinned crystal with the use of an X-ray diffraction method;
   (b) first computing means for finding respective real-space unit lattices of the plural components of the twinned crystal based on the crystal orientation matrices and for creating display data for displaying three-dimensionally the real-space unit lattices with an alterable viewpoint on a screen expressing three-dimensional real space;
   (c) second computing means for finding respective reciprocal-space primitive lattices of the plural components of the twinned crystal based on the crystal orientation matrices and for creating display data for displaying three-dimensionally the reciprocal-space primitive lattices with an alterable viewpoint on a screen expressing three-dimensional reciprocal space;

(d) third computing means for finding respective reciprocal lattice points of the plural components of the twinned crystal based on the crystal orientation matrices and for creating display data for displaying three-dimensionally reciprocal lattice points causing X-ray diffraction among the found reciprocal lattice points, with a distinction between the components of the twinned crystal, with an alterable viewpoint on the screen expressing the three-dimensional reciprocal space; and (e) a display for displaying the display data created by the first computing means, the second computing means and the third computing means.

2. An apparatus according to claim 1, wherein the third computing means creates the display data for displaying the reciprocal lattice points causing X-ray diffraction with different colors between the components of the twinned crystal.

3. An apparatus according to claim 2, wherein when diffraction spots coming from different components of the twinned crystal overlap each other, the third computing means creates the display data for displaying overlapped diffraction spots with a color different from the colors of the components of the twinned crystal.

4. An apparatus according to claim 1, wherein:
(f) the first computing means creates display data in which the real-space unit lattice is rotated around a specific axis on the screen expressing the three-dimensional real space;
(g) the second computing means creates display data in which the reciprocal-space primitive lattice is rotated around a specific axis on the screen expressing the three-dimensional reciprocal space; and
(h) the third computing means creates (h1) display data in which the reciprocal lattice points causing X-ray diffraction are rotated around a specific axis on the screen expressing the three-dimensional reciprocal space, (h2) display data in which the reciprocal lattice points causing X-ray diffraction are scaled up or scaled down on the screen expressing the three-dimensional reciprocal space, and (h3) display data in which the reciprocal lattice points causing X-ray diffraction are translated on the screen expressing the three-dimensional reciprocal space.

5. An apparatus according to claim 4, wherein the third computing means creates the display data for displaying the reciprocal lattice points causing X-ray diffraction with different colors between the components of the twinned crystal.

6. An apparatus according to claim 5, wherein when diffraction spots coming from different components of the twinned crystal overlap each other, the third computing means creates the display data for displaying overlapped diffraction spots with a color different from the colors of the components of the twinned crystal.

7. An apparatus according to claim 1, wherein:
(f) the first computing means creates (f1) display data in which the real-space unit lattice is rotated around a specific axis on the screen expressing the three-dimensional real space, (f2) display data in which the real-space unit lattice is scaled up or scaled down on the screen expressing the three-dimensional real space, and (f3) display data in which the real-space unit lattice is translated on the screen expressing the three-dimensional real space;
(g) the second computing means creates (g1) display data in which the reciprocal-space primitive lattice is rotated around a specific axis on the screen expressing the three-dimensional reciprocal space, (g2) display data in which the reciprocal-space primitive lattice is scaled up or scaled down on the screen expressing the three-dimensional reciprocal space, and (g3) display data in which the reciprocal-space primitive lattice is translated on the screen expressing the three-dimensional reciprocal space; and (h) the third computing means creates (h1) display data in which the reciprocal lattice points causing X-ray diffraction are rotated around a specific axis on the screen expressing the three-dimensional reciprocal space, (h2) display data in which the reciprocal lattice points causing X-ray diffraction are scaled up or scaled down on the screen expressing the three-dimensional reciprocal space, and (h3) display data in which the reciprocal lattice points causing X-ray diffraction are translated on the screen expressing the three-dimensional reciprocal space.

8. An apparatus according to claim 7, wherein the third computing means creates the display data for displaying the reciprocal lattice points causing X-ray diffraction with different colors between the components of the twinned crystal.

9. An apparatus according to claim 8, wherein when diffraction spots coming from different components of the twinned crystal overlap each other, the third computing means creates the display data for displaying overlapped diffraction spots with a color different from the colors of the components of the twinned crystal.

10. An apparatus according to claim 1, wherein:
(f) the first computing means creates display data in which the real-space unit lattice is shown with an altered visual axis on the screen expressing the three-dimensional real space;
(g) the second computing means creates display data in which the reciprocal-space primitive lattice is shown with an altered visual axis on the screen expressing the three-dimensional reciprocal space; and
(h) the third computing means creates (h1) display data in which the reciprocal lattice points causing X-ray diffraction are shown with an altered visual axis on the screen expressing the three-dimensional reciprocal space, (h2) display data in which the reciprocal lattice points causing X-ray diffraction are shown with a variable ratio of a magnitude of a reciprocal lattice vector to a size of the screen on the screen expressing the three-dimensional reciprocal space, and (h3) display data in which the reciprocal lattice points causing X-ray diffraction are shown with a position of origin of the reciprocal space movable relative to a center of the screen on the screen expressing the three-dimensional reciprocal space.

11. An apparatus according to claim 10, wherein the third computing means creates the display data for displaying the reciprocal lattice points causing X-ray diffraction with different colors between the components of the twinned crystal.

12. An apparatus according to claim 11, wherein when diffraction spots coming from different components of the twinned crystal overlap each other, the third computing means creates the display data for displaying overlapped diffraction spots with a color different from the colors of the components of the twinned crystal.

13. An apparatus according to claim 1, wherein:
(f) the first computing means creates (f1) display data in which the real-space unit lattice is shown with an altered visual axis on the screen expressing the three-dimensional real space, (f2) display data in which the real-space unit lattice is shown with a variable ratio of a magnitude of a real lattice vector to a size of the screen on the screen expressing the three-dimensional real space, and (f3) display data in which the real-space unit lattice is shown with a position of origin of the real space movable relative to a center of the screen on the screen expressing the three-dimensional real space;

(g) the second computing means creates (g1) display data in which the reciprocal-space primitive lattice is shown with an altered visual axis on the screen expressing the three-dimensional reciprocal space, (g2) display data in which the reciprocal-space primitive lattice is shown with a variable ratio of a magnitude of a reciprocal lattice vector to a size of the screen on the screen expressing the three-dimensional reciprocal space, and (g3) display data in which the reciprocal-space primitive lattice is shown with a position of origin of the reciprocal space movable relative to a center of the screen on the screen expressing the three-dimensional reciprocal space; and (h) the third computing means creates (h1) display data in which the reciprocal lattice points causing X-ray diffraction are shown with an altered visual axis on the screen expressing the three-dimensional reciprocal space, (h2) display data in which the reciprocal lattice points causing X-ray diffraction are shown with a variable ratio of a magnitude of a reciprocal vector to a size of the screen on the screen expressing the three-dimensional reciprocal space, and (h3) display data in which the reciprocal lattice points causing X-ray diffraction are shown with a position of origin of the reciprocal space movable relative to a center of the screen on the screen expressing the three-dimensional reciprocal space.

14. An apparatus according to claim 13, wherein the third computing means creates the display data for displaying the reciprocal lattice points causing X-ray diffraction with different colors between the components of the twinned crystal.

15. An apparatus according to claim 14, wherein when diffraction spots coming from different components of the twinned crystal overlap each other, the third computing means creates the display data for displaying overlapped diffraction spots with a color different from the colors of the components of the twinned crystal.

16. A method for analyzing a twinned crystal, using an apparatus for analyzing a twinned crystal, the method comprising:

(a) obtaining, by using X-ray single crystal structure analytical equipment, respective crystal orientation matrices of plural components of the twinned crystal with the use of an X-ray diffraction method;

(b) finding respective real-space unit lattices of the plural components of the twinned crystal based on the crystal orientation matrices and creating first display data for displaying three-dimensionally the real-space unit lattices with an alterable viewpoint on a screen expressing three-dimensional real space;

(c) finding respective reciprocal-space primitive lattices of the plural components of the twinned crystal based on the crystal orientation matrices and creating second display data for displaying three-dimensionally the reciprocal-space primitive lattices with an alterable viewpoint on a screen expressing three-dimensional reciprocal space;

(d) finding respective reciprocal lattice points of the plural components of the twinned crystal based on the crystal orientation matrices and creating third display data for displaying three-dimensionally reciprocal lattice points causing X-ray diffraction among the found reciprocal lattice points, with a distinction between the components of the twinned crystal, with an alterable viewpoint on the screen expressing the three-dimensional reciprocal space; and (e) displaying, on a display of the apparatus for analyzing a twinned crystal, the first display data, the second display data, and the third display data.

17. A method according to claim 16, wherein the reciprocal lattice points causing X-ray diffraction are displayed on the display with different colors between the components of the twinned crystal.

18. A method according to claim 17, wherein when diffraction spots coming from different components of the twinned crystal overlap each other, overlapped diffraction spots are displayed on the display with a color different from the colors of the components of the twinned crystal.

* * * * *